United States Patent [19]

Fisher et al.

[11] Patent Number: 5,534,520

[45] Date of Patent: Jul. 9, 1996

[54] SPIRO COMPOUNDS CONTAINING FIVE-MEMBERED RINGS

[76] Inventors: Abraham Fisher, 47/7 David Elazar Street, Holon; Yishai Karton, 8 Ben-Gurion Street, Ness-Ziona; Daniele Marciano, 22 Usichkin Street, Ramat-Hasharon; Dov Barak, 20 Usichkin Street, Rehovot; Haim Meshulam, 13 Harishonim Street, Bat-Yam, all of Israel

[21] Appl. No.: 94,855

[22] Filed: Jul. 20, 1993

Related U.S. Application Data

[63] Continuation-in-part of Ser. No. 685,397, Apr. 9, 1991, abandoned, which is a continuation-in-part of Ser. No. 507,708, Apr. 10, 1990, abandoned.

[51] Int. Cl.$^6$ .................... A61K 31/445; C07D 221/20; C07D 491/10; C07D 491/20

[52] U.S. Cl. ............................ 514/278; 546/16; 546/19; 546/20

[58] Field of Search ................................ 546/16, 19, 20; 514/278

[56] References Cited

U.S. PATENT DOCUMENTS

| | | | |
|---|---|---|---|
| 3,161,644 | 12/1964 | Janssen | 546/215 |
| 3,850,949 | 11/1974 | Ono et al. | 548/240 |
| 5,073,560 | 12/1991 | Wu et al. | 514/278 |

FOREIGN PATENT DOCUMENTS

| | | | |
|---|---|---|---|
| 273659A1 | 7/1988 | European Pat. Off. | 546/16 |
| 412821A2 | 2/1991 | European Pat. Off. | 546/19 |
| 452101 | 10/1991 | European Pat. Off. | |
| 2252612 | 5/1973 | Germany | 546/19 |
| 2164882 | 6/1990 | Japan | 546/19 |

OTHER PUBLICATIONS

E. Galvez, et al., Synthesis and Stuctural Study of Cyclopenatne, Indene and Flourene Spiro-derivatives, Journal of Heterocyclic Chemistry, 20, 13, 1983.

P. L. Feldman, et al., A Novel Route to the Class of Analgetics Journal of Organic Chemistry, 55, 4207–4209, 1990.

(List continued on next page.)

*Primary Examiner*—Alan L. Rotman
*Attorney, Agent, or Firm*—Darby & Darby

[57] ABSTRACT

Compounds useful for treating diseases of the central or peripheral nervous system in mammals have formulae I–XIII:

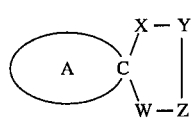

I

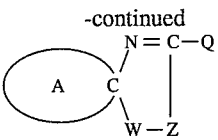

II

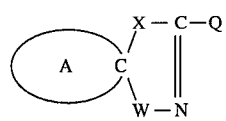

III

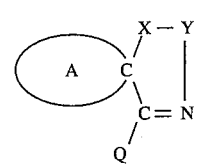

IV

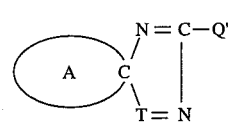

V

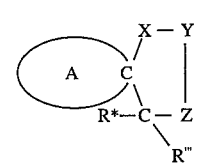

VI

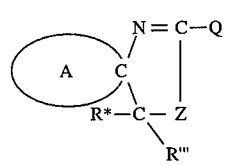

VII

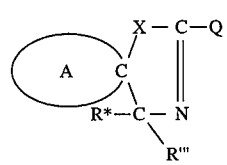

VIII

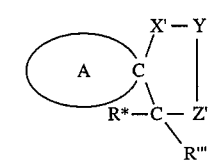

IX

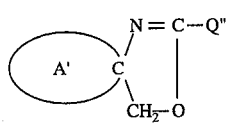

X

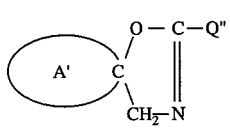

XI

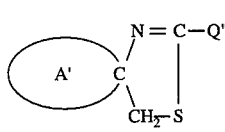

XII (Abstract continued on next page.)

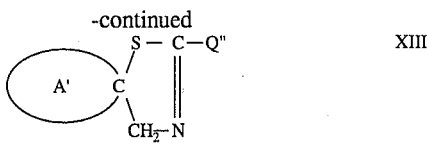

XIII wherein ring A or A' together with the spiro-carbon atom constitutes a bridged or unbridged ring containing one or two ring nitrogen atoms; and the other symbols have specified values, subject to certain conditions.

32 Claims, No Drawings

OTHER PUBLICATIONS

Y. Ishihara, et al., Central Cholinergic Agents. III. Synthesis of 2–Alkoxy–2,8–diazaspiro[4.5]decane–1,3–diones as Muscarinic Agonists, Chem. Pharm. Bull., 40(5), 1177–1185, 1992.
Nordvall, G., Analogues of the Muscarinic Agent 2–Methylspiro[1–azabicyclo[2.2.2.]octane–3,4–[1,3]dioxolane]: Synthesis and pharmacology, J. Med. Chem., 1992, 35, 1541–1550.
Abstract of TW 201312 (State of Israel Inst. Biol. Res.) Mar. 1, 1993.
J. Saunders, 2–Methyl–1,3–dioxaazaspiro (4,5)decanes as Novel Muscarinic Cholinergic Agonists, Journal of Medical Chemistry, 31, 486–491, 1988.
Journal of Medicinal Chemistry, vol. 12, p. 920, 1969.
Journal of Medicinal Chemistry, 1970, p. 307.
G. M. Carrera, Jr., et al., Synthesis of Novel Substituted Spirohydantoins, Journal of Heterocyclic Chemistry, 29, 847–85 1992.
G. G. Trigo, et al., PMR and 13C–NMR Spectroscopy of Tropane an N–Substituted Nortopane Spirohydantoins, Journal of Pharmaceutical Sciences, 70(1), 87–89, 1981.
G. G. Trigo, et al., H NMR Study of the Preferred Conformations in N–Alkygranatanine–3–spiro–5'–hydantoins, Journal of Heterocyclic Chemistry, 15, 833–837, 1978.
G. G. Trigo, et al., Synthesis ans Structural Study of Quinuclidine Spiro Derivatives, Journal of Heterocyclic Chemistry, 18, 1507–1511, 1981.
M. V. Garcia, et al., Study of the Reaction Between Cyanohydrin and Chlorosulfonyl Isocyanate. A New, Efficient Method for the One–Pot Synthesis of 2,4–Oxazolidinediones, Synthesis, 1991.
A. Jossang, et al. Horsfiline, an Oxindole Alkaloid from Horsfieldia superba, Journal of Organic Chemistry, 56, 6527–6530, 1991.
Chem. Abstracts, vol. 71 (19) 91359–d, Nov. 10, 1969.
Chem. Abstracts, vol. 73 (19), 98869–v, Nov. 9, 1970.
Chem. Abstracts, vol. 97(17), 144165H, Oct. 25, 1982.
Chem. Abstracts, vol. 109 (3) 16597–e Jul. 18, 1988.
Trigo et al, Journal of Heterocyclic Chemistry, vol. 21, No. 5 pp. 1479–1483 Sep.–Oct. 1984.
Chemical Abstracts 119: 160165m Oct. 11, 1993.
Chemical Abstracts 119: 101570f Aug. 1993.
Chemical Abstracts 119: 101573j Aug. 1993.
Chemical Abstracts 119: 140115j Sep. 27, 1993.
Chemical Abstracts 114: 164201q Apr. 29, 1991.
Chemical Abstracts 110: 114821p Mar. 27, 1989.
Chemical Abstracts 110: 140112f Apr. 17, 1989.
Chemical Abstracts 110: 140094y Apr. 17, 1989.
Chemical Abstracts 110: 140152u Apr. 17, 1989.
Chemical Abstracts 110: 101632c Mar. 20, 1989.

SPIRO COMPOUNDS CONTAINING FIVE-MEMBERED RINGS

This application is a continuation-in-part of Ser. No. 07/685,397 filed Apr. 9, 1991, now abandoned, which is a Continuation-in-part of Ser. No. 507,708 filed Apr. 10, 1990, now abandoned.

FIELD AND BACKGROUND OF THE INVENTION

The present invention relates to spiro five-membered ring compounds in which the ring which is spiro-connected to the five-membered ring as set forth herein is a saturated bridged or unbridged ring containing one or two nitrogen atoms; to pharmaceutical compositions containing the spiro compounds and to a method for treating diseases of the central and peripheral nervous system using such spiro-compounds or pharmaceutical compositions.

Novel spiro-quinuclidine compounds, in which oxathiolane rings were connected in spiro manner with quinuclidine rings, were described e.g. in European Patent Application No. 0205247 A2, published Dec. 17, 1986, and in U.S. Pat. Nos. 4,855,290 (issued Aug. 8, 1989), 4,981,858 (issued Jan. 1, 1991), 4,900,830 (issued Feb. 13, 1990) and 4,876,260 (issued Oct. 24, 1989). Similarly, some spiro-oxazolines have been described in U.S. Pat. No. 5,053,412 (issued Oct. 5,053,412), while some spiro-oxazolines and some spiro-thiazolines have been described in U.S. patent application Ser. No. 07/685,379. It is to be understood that the entire contents of the above-mentioned patents and of U.S. Ser. No. 07/685,379, as well as any other patents and literature articles mentioned in the present patent application are incorporated herein by reference. The novel compounds of the above-mentioned patents were found to possess central nervous system activity. The biological activity of the compound 2-methylspiro(1,3-oxathiolane-5,3)quinuclidine, which exists as geometrical cis- and trans-isomers depending upon whether the 2-methyl group is located on the same side of the oxathiolane ring as the quinuclidine ring nitrogen atom (cis) or on the other side of the quinuclidine ring nitrogen atom (trans), was in particular extensively investigated, and it was found on the basis of pre-clinical tests that the cis- compound (code no. AF102B) was especially promising for the control of senile dementia of Alzheimer's type (SDAT). It is also of interest that each of the cis- and trans-isomers may be optically resolved, and the biological activity of the optical isomers was also investigated in a number of cases.

It is a principal object of the invention to provide novel spiro-compounds. Further objects of the invention, and especially those which relate to the provision of useful pharmaceutical compositions and methods for the treatment of disease, will be apparent from the description which follows.

SUMMARY OF INVENTION

The present invention provides, in one aspect, novel compounds of formulae I, II, III, IV, V, VI, VII, VIII and IX

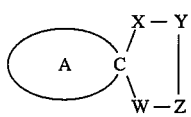   I

-continued

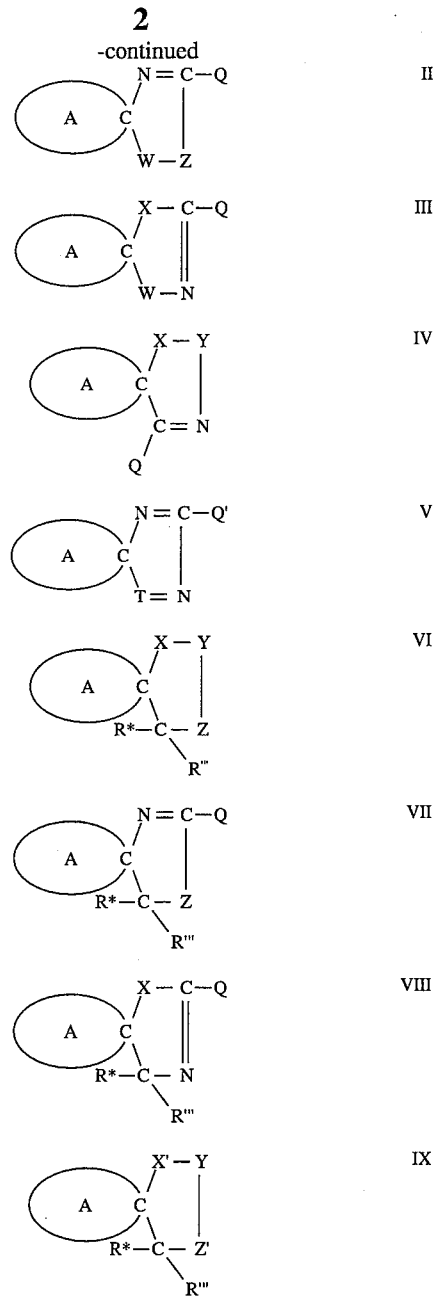

and their pharmaceutically acceptable salts, enantiomers and racemates, wherein ring A together with the spiro-carbon atom constitutes a bridged or unbridged ring containing one or two ring nitrogen atoms; X is >O,>S or >NR°; T is —C(Q)= or —N=; Y is >C=O, >C=S, >C=NR° >C=CRR', >CRR', >CHOR", >O, >S or >NR°; Z is >O, >S, >C=O, >C=S, >C=NR° >C=CRR', >CRR', >CHOR" or >NR°; W is >O, >S, >C=O, >C=S, >C=NR° >C=CRR', >CHOR" or >NR°; Q and Q' are each independently selected from OR, SR, NRR' and R; X' and Z' are each independently selected from >C=O, >C=S and >C=CRR'; and R, R', R", R°, R* and R''' are each independently selected from H, $C_{1-6}$ alkyl, $C_{1-6}$ alkoxy, $C_{2-6}$ hydroxyalkyl, $C_{2-6}$ alkenyl, $C_{2-6}$ alkynyl, phenyl and $C_{1-6}$ alkyl substituted by one, two or three phenyls, while R" and R° may also be independently selected from $C_{1-6}$ alkanoyl;

provided that the depicted five-membered ring contains at least one ring carbon atom in addition to the spiro-carbon atom, that no two adjacent ring atoms are simultaneously oxygen atoms, and that: (ia) in formula I, —W—Z—Y—X— is neither —C(=O)—NH—C(=O)—N(alkyl)—, nor —C(=O)—NH—C(=O)—NH—, (ib) in formula I when —W—Z—Y—X— is —C(=O)—NH—C(=O)—O—, then ring A is not the quinuclidine ring, (ii) in formula I, when —W—Z—Y—X— is —NH—C(=O)—N(Ph)—NH—, —NH—N(Ph)—C(=O)—NH—, —NR°—NR°—C(=O)—NR°—, —NR°—NR°—C(=S)—NR°—, or —O—CH$_2$—C(CH$_3$)$_2$—NH—, then ring A is not an N-methylpiperidine ring, and when —W—Z—Y—X— is —NR°—NR°—C(=S)—NR°—, then ring A is also not an unsubstituted piperidine ring, (iiia) in formula III, ring A may not be substituted by two phenyl radicals, (iiib) in formula III, when Q is NRR' and W is C=O, then X is not O, (iv) in formula VI when Y is CRR' and either X=Z=O or S, or one of X and Z is O and the other is S, then at least one of R* and R'''≠H, (v) in formula VI when Y is CRR', X is O or S and ring A is a piperidine ring, then Z is NR°, (vi) in formula VI when X is O, Y is NR° and Z is C=O or C=S, then either ring A is a bridged ring or at least one of R* and R''' is not H, (vii) in formula VI when —X—Y—Z— is —O—C(=O)—NH—, —O—C(=S)—NH—, —O—NR°—C(=O)— or —O—NR°—C(=S)—, and R° is H or alkyl, then ring A is not a piperidine ring, (viii) in formula VII when Z is O, then either Q is SR or NRR', or at least one of R* and R''' is not H, (ix) in formula VIII when X is O or S, then either Q is SR, or at least one of R* and R''' is not H, and (x) in formula IX when —X'—Y—Z'— is —C(=O)—NR°—C(=O)—, and R° is H or alkyl, then ring A is not a piperidine ring.

In a particular embodiment of the invention, ring A may be selected from among the group of structures K, L, M, N, P and S, namely:

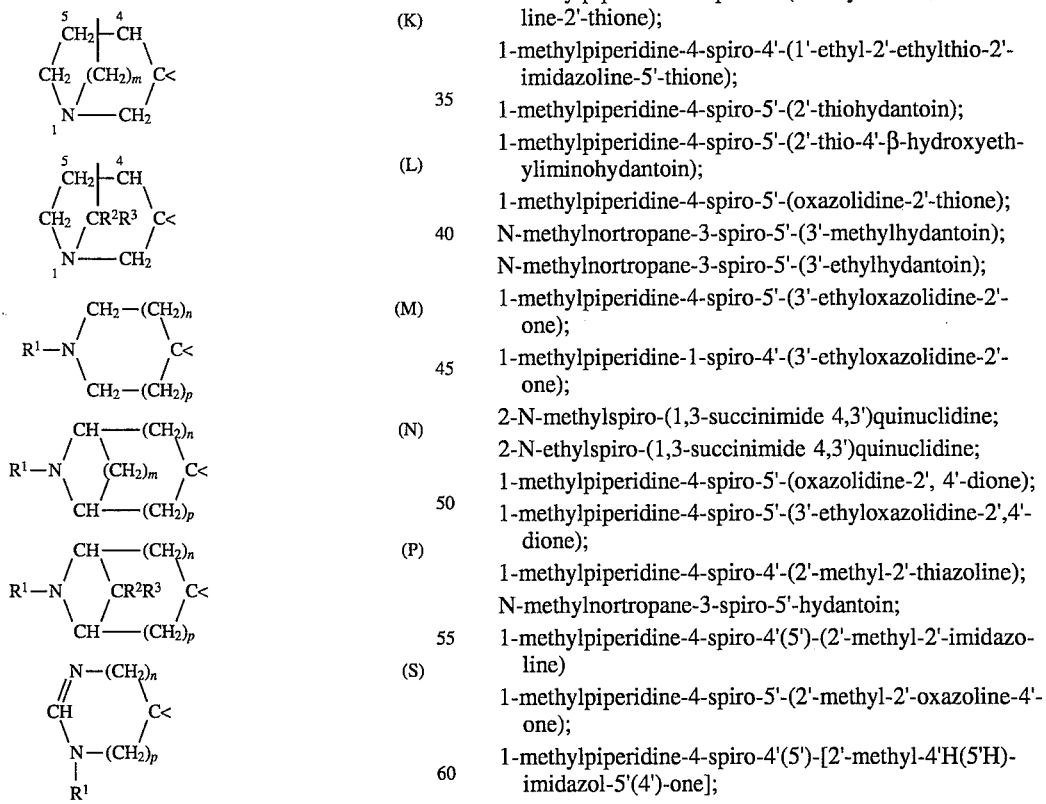

wherein each such structure is unsubstituted or is substituted by 1–3 substituents selected from C$_{1-6}$ alkyl and hydroxyl, in structures K and L the bridge is attached at one end to position 1 and at the other end to position 4 or 5, m is 1, 2 or 3, and n and p are each independently 0, 1, 2 or 3, provided that n+p=1–3; R$^1$ is selected from hydrogen, C$_{1-6}$-alkyl, C$_{2-6}$-alkenyl, C$_{2-6}$-alkynyl, C$_{3-7}$— cycloalkyl, C$_{1-6}$-alkyl substituted by 1–6 halogen atoms, hydroxy-C$_{1-6}$-alkyl, C$_{1-6}$-alkoxy, C$_{1-6}$-alkylthio, C$_{1-6}$-alkoxy-C$_{1-6}$-alkyl, carboxy-C$_{1-6}$-alkyl, (C$_{1-6}$-alkoxy)carbonyl-C$_{1-6}$-alkyl, amino-C$_{1-6}$-alkyl, mono-(C$_{1-6}$-alkyl)amino-C$_{1-6}$-alkyl, di-(C$_{1-6}$-alkyl)amino-C$_{1-6}$-alkyl, 2-oxo-pyrrolidin-1-yl-methyl, aryl, diarylmethylol, C$_{1-6}$-alkyl substituted by one or two aryl groups, C$_{1-6}$-alkanoyl and arylcarbonyl; and aryl denotes unsubstituted phenyl or phenyl substituted by 1–3 substituents selected from halogen, C$_{1-6}$-alkyl, C$_{1-6}$-alkoxy and CF$_3$, and R$^2$ and R$^3$ are independently selected from C$_{1-4}$ alkyl.

Exemplary compounds provided by the invention are the following:

1-methylpiperidine-4-spiro-5'-(3'-ethylhydantoin);
1-methylpiperidine-4-spiro-5'-(1'-acetylhydantoin);
piperidine-4-spiro-5'-(3'-ethylhydantoin);
1-methylpiperidine-4-spiro-5'-(3'-methylhydantoin);
piperidine-4-spiro-5'-(3'-methylhydantoin);
1-methylpiperidine-4-spiro-5'-(3'-propargylhydantoin);
1-methylpiperidine-4-spiro-4'-(2',5'-bis(methylthio)-4'H-imidazole);
1-methylpiperidine-4-spiro-5'-(3'-ethyl-4'-thiohydantoin);
1-methylpiperidine-4-spiro-5'-(4'-methylthio-3'-imidazoline-2'-thione);
1-methylpiperidine-4-spiro-5'-(2',4'-dithiohydantoin);
1-methylpiperidine-4-spiro-5'-(3'-ethyl-2',4'-dithiohydantoin);
1-methylpiperidine-4-spiro-5'-(4'-ethylthio-3'-imidazoline-2'-thione);
1-methylpiperidine-4-spiro-4'-(1'-ethyl-2'-ethylthio-2'-imidazoline-5'-thione);
1-methylpiperidine-4-spiro-5'-(2'-thiohydantoin);
1-methylpiperidine-4-spiro-5'-(2'-thio-4'-β-hydroxyethyliminohydantoin);
1-methylpiperidine-4-spiro-5'-(oxazolidine-2'-thione);
N-methylnortropane-3-spiro-5'-(3'-methylhydantoin);
N-methylnortropane-3-spiro-5'-(3'-ethylhydantoin);
1-methylpiperidine-4-spiro-5'-(3'-ethyloxazolidine-2'-one);
1-methylpiperidine-1-spiro-4'-(3'-ethyloxazolidine-2'-one);
2-N-methylspiro-(1,3-succinimide 4,3')quinuclidine;
2-N-ethylspiro-(1,3-succinimide 4,3')quinuclidine;
1-methylpiperidine-4-spiro-5'-(oxazolidine-2', 4'-dione);
1-methylpiperidine-4-spiro-5'-(3'-ethyloxazolidine-2',4'-dione);
1-methylpiperidine-4-spiro-4'-(2'-methyl-2'-thiazoline);
N-methylnortropane-3-spiro-5'-hydantoin;
1-methylpiperidine-4-spiro-4'(5')-(2'-methyl-2'-imidazoline)
1-methylpiperidine-4-spiro-5'-(2'-methyl-2'-oxazoline-4'-one);
1-methylpiperidine-4-spiro-4'(5')-[2'-methyl-4'H(5'H)-imidazol-5'(4')-one];
1-methylpiperidine-4-spiro-4'-(2'-methylthio-5'-methoxy-4'H-imidazole;
1-methylpiperidine-4-spiro-4'-(2'-methylthio-5'-amino-4'H-imidazole;
1-methylpiperidine-4-spiro-4'-(2'-methylthio-5'-aminomethyl-4'H-imidazole;

1-methylpiperidine-4-spiro-4'-(2',5'-bis(aminomethyl)-4'H-imidazol).

The present invention moreover provides a pharmaceutical composition for use in treating diseases of the central and peripheral nervous system in mammals, which comprises an amount effective for use in treating said diseases, of at least one compound having one of the formulae I, II, III, IV, V, VI, VII, VIII and IX as defined above, including their pharmaceutically acceptable salts, enantiomers and racemates, together with at least one pharmaceutically acceptable diluent, carrier or adjuvant. Such composition is preferably in a form suitable for oral, rectal, parenteral or transdermal administration (in this case the composition may comprise additionally a low molecular weight fatty acid), or for administration by insufflation or nasal spray, and may be in unit dosage form. The at least one compound of the invention as defined above, may be present in the unit dosage in an amount in the range of, e.g. about 0.5 to about 100 mg, preferably about 5 to about 100 mg, more preferably about 10 to about 50 mg.

According to a particular embodiment of the invention, the pharmaceutical composition as described in the preceding paragraph may comprise additionally at least one further pharmacologically active compound selected from physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine, propantheline, methantheline, glycopyrrolate, tropenzilium, nortriptyline, amitriptyline, imipramine, minaprine, secoverine, AFDX-116, nicotine, alaproclate, zimelidine, deprenyl and Nerve Growth Factor.

The present invention also provides a method for treating diseases of the central or peripheral nervous system in mammals, which comprises administering thereto an amount effective for use in treating said diseases, of at least one compound having one of the formulae I, II, III, IV, V, VI, VII, VIII and IX as defined above, including their pharmaceutically acceptable salts, enantiomers, tautomers and racemates. Such compounds may of course be utilized for this purpose in the form of a pharmaceutical composition according to the invention, as defined above.

The present invention relates furthermore to compounds as disclosed in incorporated-by-reference U.S. Ser. No. 07/685,379, (to which particular reference may be made for preparative details and biological properties), of the following formulae X, XI, XII and XIII

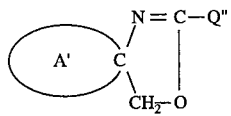

X

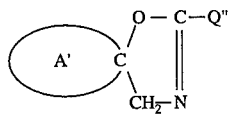

XI

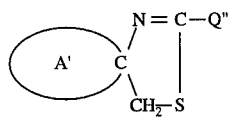

XII

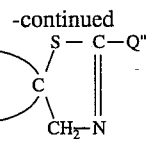

XIII including enantiomers, racemates and pharmaceutically acceptable acid addition and quaternary salts thereof, wherein ring A', together with the depicted spiro carbon atom, is selected from the structures M, N and P, namely:

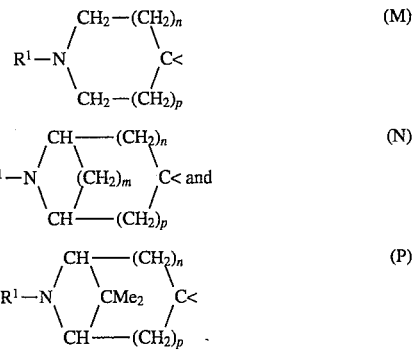

wherein each such structure is unsubstituted or is substituted by methyl or hydroxyl, m is 1, 2 or 3, and n and p are each independently 0, 1, 2 or 3, provided that n+p=1–3; Q" is selected from hydrogen, $NH_2$, $NH-C_{1-6}$-alkyl, $N(C_{1-6}$-alkyl$)_2$, $C_{1-6}$-alkyl, $C_{2-6}$-alkenyl, $C_{2-6}$-alkynyl, $C_{3-7}$-cycloalkyl, $C_{1-6}$-alkyl substituted by 1–6 halogen atoms, hydroxy-$C_{1-6}$-alkyl, $C_{1-6}$-alkoxy, $C_{1-6}$-alkylthio, $C_{1-6}$-alkoxy-$C_{1-6}$-alkyl, carboxy-$C_{1-6}$-alkyl, ($C_{1-6}$-alkoxy)carbonyl-$C_{1-6}$-alkyl, amino-$C_{1-6}$-alkyl, mono-($C_{1-6}$-alkyl)amino-$C_{1-6}$-alkyl, di-($C_{1-6}$-alkyl)amino-$C_{1-6}$-alkyl, 2-oxo-pyrrolidin-1-yl-methyl, aryl, diarylmethylol, $C_{1-6}$-alkyl substituted by one or two aryl groups; $R^1$ is independently selected from the groups from which Q" is selected and $C_{1-6}$-alkanoyl and arylcarbonyl; and aryl denotes unsubstituted phenyl or phenyl substituted by 1–3 substituents selected from halogen, $C_{1-6}$-alkyl, $C_{1-6}$-alkoxy and $CF_3$, provided that in formula XI, when ring A', together with the depicted spiro carbon atom, is structure M which is unsubstituted, then when n=p=1 and Q" is $NH_2$, $R^1$ is not methyl. The present invention further contemplates the possibility of replacing the $CMe_2$ bridge in structure (P) above more generally by a $CR^2R^3$ bridge, where $R^2$ and $R^3$ are independently selected from $C_{1-4}$ alkyl.

Preferred such compounds are those where Q" is selected from the group consisting of hydrogen, $NH-C_{1-6}$-alkyl, $N(C_{1-6}$-alkyl$)_2$, $C_{1-6}$-alkyl and aryl, and $R^1$ is hydrogen or methyl, such as, for example:

1-methylpiperidine-4-spiro-4'-(2'-methyl-2'-oxazoline),
1-methylpiperidine-4-spiro-4'-(2'-ethyl-2'-oxazoline),
1-methylpiperidine-4-spiro-5'-(2'-methyl-2'-oxazoline),
1-methylpiperidine-4-spiro-5'-(2'-ethyl-2'-oxazoline),
1-methylpiperidine-4-spiro-5'-(2'-methyl-2'-thiazoline),
including the acid addition and quaternary salts thereof.

The invention also provides, in a particular embodiment, compounds of any of the formulae I through IX or X through XIII as defined herein (and a related pharmaceutical composition and method of treatment), having the molecular dimensions indicated below, where: r is a reference point defined by the position of an anion corresponding to the cationic form of a non-doubly-bonded nitrogen atom, defined as N*, of ring A (or A') in such compound in its most stable conformation, X* defines a ring hetero atom in the depicted 5-membered ring having any of the formulae I through IX, or X through XIII, such ring hetero atom being in a position adjacent to the spiro carbon atom, Z* defines the next but one ring atom from X* in the depicted 5-membered ring, and Q* defines the terminal carbon or nitrogen atom of a side-chain attached to the ring atom between atoms X* and Z* in the depicted 5-membered ring, side-chain hydrogen atoms being ignored for this purpose; such molecular dimensions having substantially the following values, namely: a dihedral angle r-X*—Q*—Z*=from −54° to −170°; and molecular distances r-N*=3.0 angstroms (the reference distance), r-X*=from 5.7 to 6.75 angstroms, r-Q*= from 7.9 to 8.90 angstroms, x-Q*=from 2.4 to 2.8 angstroms; such compounds having the thus-defined molecular dimensions being characterized by having muscarinic agonist activity. This definition based on molecular dimensions is supported by biological tests, see especially Table 1, below.

In another embodiment, the invention provides a pharmaceutical composition which comprises at least one compound of any of the formulae I through IX or X through XIII as defined herein (and a related method of treatment), and additionally Nerve Growth Factor, the at least one compound according to claim 1 being present in an amount which promotes the nerve growth activity of the Nerve Growth Factor. For support for this embodiment of the invention, see especially Test No. 5, detailed below. It may be note that the compounds according to the present invention, unlike certain known compounds possessing central or peripheral nervous system activity, do not per se promote nerve growth activity in absence of Nerve Growth Factor, thus allowing better control, when nerve growth promotion is desired in therapy.

DETAILED DESCRIPTION OF THE INVENTION

The methods used for preparing compounds of the invention are those which are essentially known to organic chemists for the formation of the five-membered rings, ring-substitution, changing the degree of ring saturation/unsaturation, interconversion of salts and bases, quaternary salt formation, and so forth. It will be appreciated, therefore, that while exemplary methods of preparing certain compounds of the invention will be described, other methods can also be applied to the preparation of the present compounds, as will be known by the skilled person.

When the desired five-membered ring is a hydantoin, for example, these compounds may be prepared by forming this ring by reacting the corresponding saturated N-heterocyclic ketone with ammonium carbonate and cyanide ions, and the 3'-N atom in the product may be substituted in known manner. These reactions may be illustrated as follows, where the N-heterocyclic ketone is exemplarily 1-methylpiperidine-4-one:

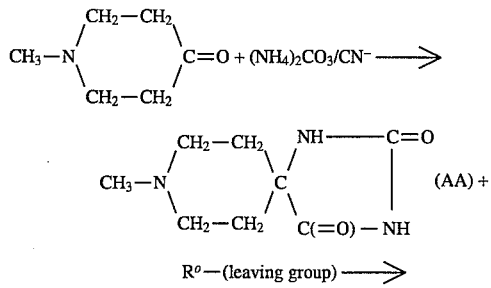

$R^o$—(leaving group) ⟶

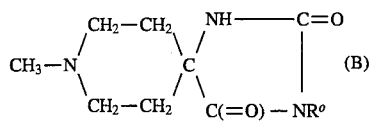

(e.g. AF160, $R^o$=Et; AF178, $R^o$=Me;
  AF185, $R^o$=propargyl;
  AF167, $R^o$=Me, analog*
  AF168, $R^o$=Et, analog*)

(*in which the N-methylpiperidine moiety contains a 2, 6-ethylene bridge i.e. the N-methylnortropane analog)

The leaving group in "$R^o$-(leaving group )" may be e.g. bromide, chloride or p-toluenesulfonate and $R^o$ is as defined herein, excepting H, alkoxy and alkanoyl. This substitution reaction may be conducted under essentially known conditions, e.g. by reacting the 3'-unsubstituted hydantoin in presence of an alkali such as KOH and using a solvent such as ethanol. The corresponding 1',3'-disubstituted compound may be obtained in the above reaction by using excess of the "$R^o$-(leaving group)" reagent, or by reacting compound (B) with "$R^o$-(leaving group)".

It may be noted that the 1-methyl group in structure (B) may be removed by reaction with a demethylating agent such as $CH_3CH(Cl)OCOCl$:

(B) + demethylating agent ⟶

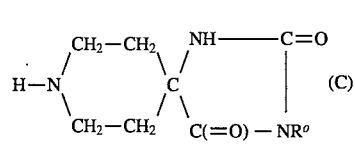

e.g. AF160(Des), $R^o$=Et
  AF179, $R^o$=Me

Reaction of compound (AA) with an alkanoyl halide or an alkanoic anhydride under standard alkanoylating conditions effects substitution in the 1'-position, thus:

(AA) + alkanoylating agent ⟶

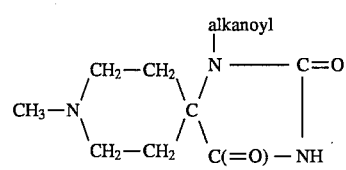

e.g. AF164, alkanoyl=acetyl

When the desired five-membered ring is a dithiohydantoin, for example, these compounds may be prepared by forming this ring by reacting the corresponding saturated N-heterocyclic ketone with cyanide ions, ammonium chloride and carbon disulfide. When effecting substitution (e.g. alkylation) reactions, which in the case of the hydantoins substitute on the N atoms, it is found that the thiohydantoins give N— and/or S— substituted products. Reference may be made to the Examples (infra) for the reaction conditions which give the different products, of mixtures of products which may be separated. These reactions may be illustrated as follows, where the N-heterocyclic ketone is exemplarily 1-methylpiperidine-4-one:

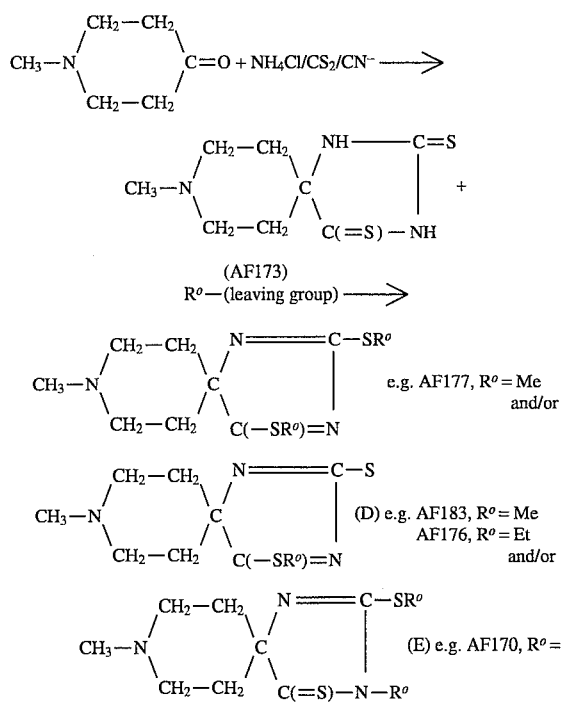

(AF173)
R°—(leaving group) ⟶ e.g. AF177, R° = Me
and/or (D) e.g. AF183, R° = Me
AF176, R° = Et
and/or (E) e.g. AF170, R° = Et The leaving group in "R°-(leaving group)" may be as described above for the hydantoins, as is the value of R°. The substitution reaction may be conducted under essentially known conditions.

Dithiohydantoins may in general also be obtained by reacting the corresponding hydantoins with phosphorus pentasulfide, for example, thus:

(B) + phosphorus pentasulfide ⟶
(AF160)

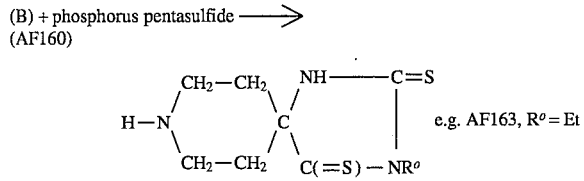

e.g. AF163, R° = Et

When compound (E) is reacted with 20% HCl, the S—R° is hydrolyzed to give the following compound:

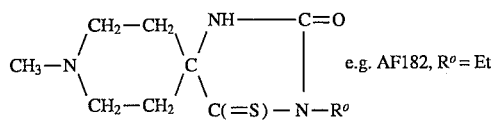

e.g. AF182, R° = Et

Similar reaction of compound (D) with 20% HCl gives a compound having the following structure (see e.g. Example 12):

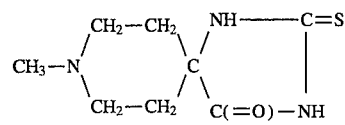

This compound is also formed by hydrolyzing a compound of formula

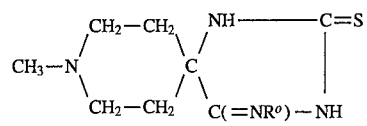

which in turn may be prepared by reacting compound AF173 with R°NH$_2$ (see e.g. Example 13, where R°-β-hydroxyethyl).

Compounds of the invention which are oxo- or thiono-substituted oxazolidines may be prepared, for example, by the following methods:

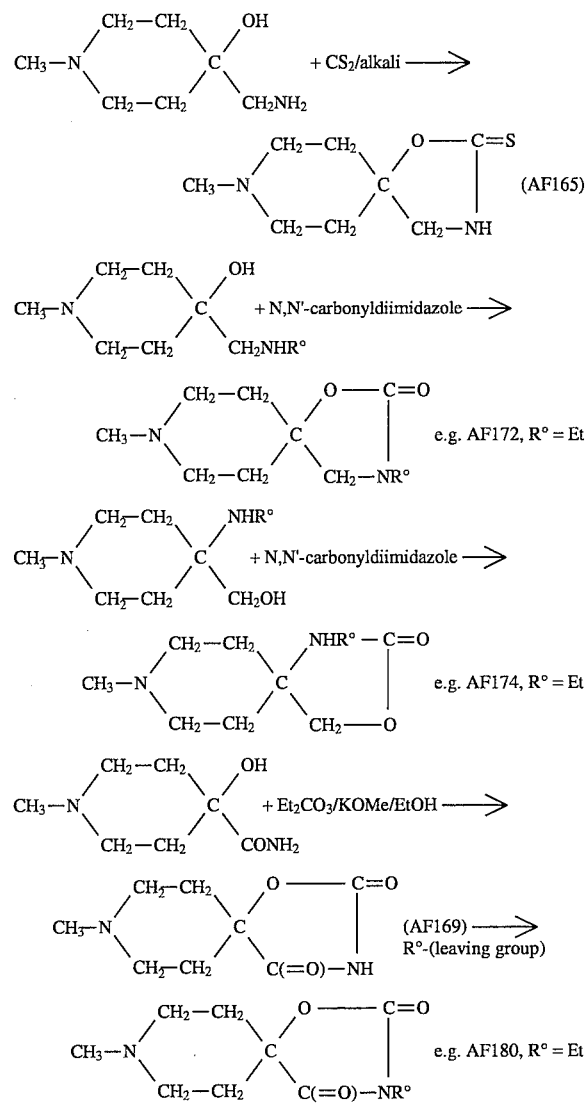

(AF165)

e.g. AF172, R° = Et e.g. AF174, R° = Et (AF169) ⟶
R°-(leaving group)

e.g. AF180, R° = Et

The leaving group in "R°-(leaving group)" may be as described above for the hydantoins, as is the value of R°. The substitution reaction may be conducted under essentially known conditions.

Compounds of the invention in which the five-membered ring is a succinimide, may be prepared, for example, as follows:

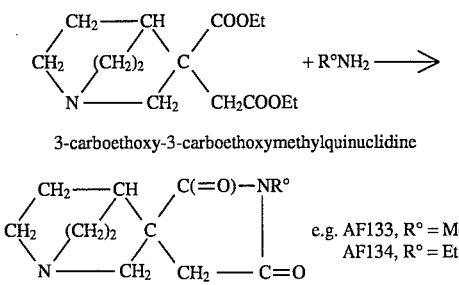

3-carboethoxy-3-carboethoxymethylquinuclidine e.g. AF133, R° = Me
AF134, R° = Et Thiazolines according to the invention may be made, for example, by the following method:

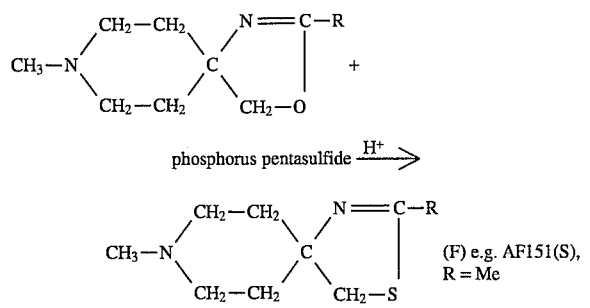

(F) e.g. AF151(S), R = Me

It may be mentioned in passing that the compound of formula

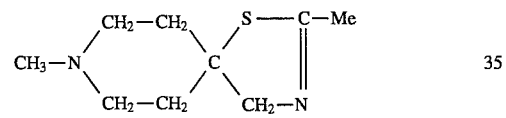

designated AF150(S), has been described in our U.S. patent application Ser. No. 07/685,379, whereas the compounds of formula (F) were not specifically exemplified in that U.S. patent application. However, it has now surprisingly been found that compounds of formula (F) as exemplified by compound AF151(S), are surprisingly much more promising from a pharmacological activity point of view, than the class of compounds exemplified by AF150(S).

Imidazolines according to the present invention may be prepared, for example, according to the following scheme:

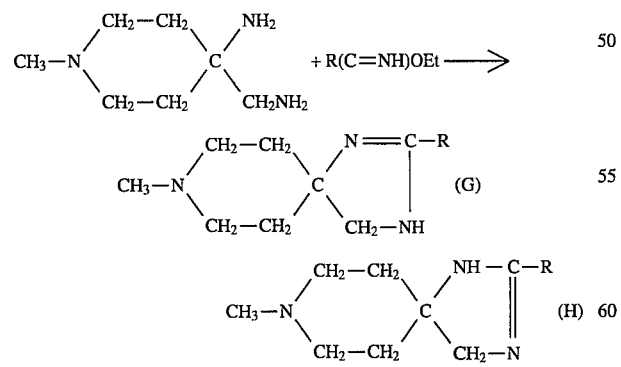

In this case the product, e.g. AF190, R=Me, may exist as a tautomeric mixture of structures (G) and (H).

The following compounds in which R and R° are as defined herein, but are each preferably, e.g., Me or Et, also constitute preferred embodiments of the compounds according to the present invention.

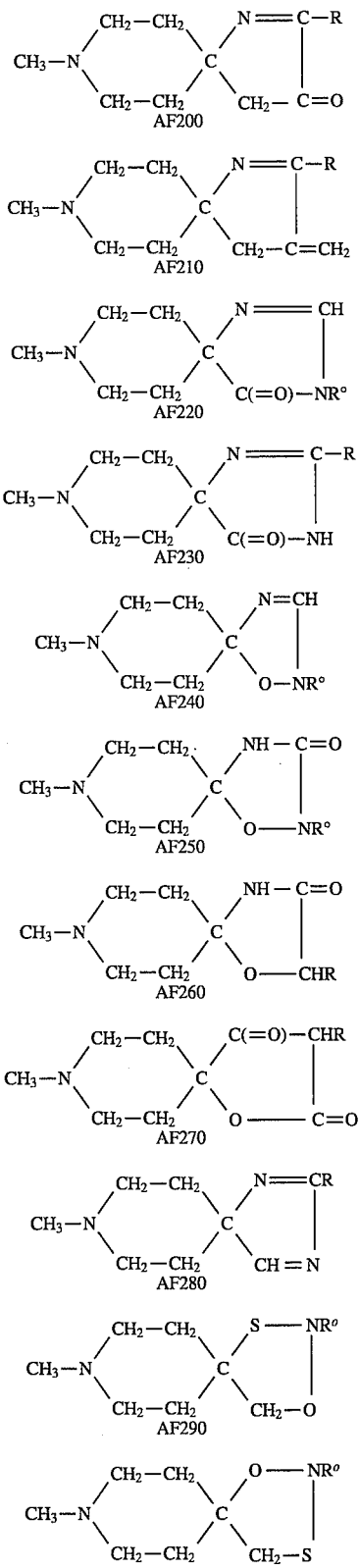

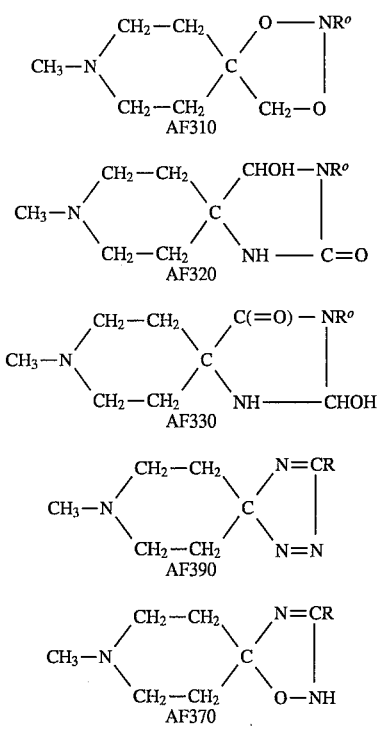

It is to be understood that whereas in the foregoing description, the illustrative compounds of the invention have shown piperidine, nortropine and quinuclidine rings, any nitrogen heterocyclic ring as defined herein as suitable for spiro-configuration with the depicted spiro five-membered ring may be substituted therefore. A similar remark applies to the practical examples, which are merely illustrative and not limitative in effect.

The spiro-compounds of the invention are in general potentially useful for the treatment of presenile and senile dementia, senile dementia of Alzheimer's type (SDAT), atypical Alzheimer's disease (Perry et al, Advances in Neurology, ads. R. J. Wurtman et al., 51:41, 1990), combined multiinfract dementia and Alzheimer's disease, age-associated memory impairments (AAMI), acute confusion disorders, emotional and attention disorders, mania, tardive-dyskinesia, hyperkinesia, mixed Alzheimer's and Parkinson's disease, aphasia, hallucinatory-paranoid states, post encephalitic amnesic syndrome, alcohol withdrawal symptoms, Huntington's chorea, Pick's disease, Friedrick's ataxia, Gilles de la Tourette disease and Down syndrome, because all of these disease states are disturbances in which a central cholinergic hypofunction has been implicated at least to a certain extent. The present compounds are moreover potentially useful for the treatment of progressive supranuclear palsy; they are also potentially analgesic agents and thus may be useful in the treatment of severe painful conditions such as rheumatism, arthritis and terminal illness.

As indicated briefly above, the spiro-compounds of the present invention may be used in combination with at least one additional pharmacologically active compound, for example, acetylcholinesterase inhibitors such as physostigmine or tetrahydroaminoacridine; in combination with acetylcholine precursors such as choline or lecithin; in addition to "nootropic" drugs such as piracetam, aniracetam, oxiracetam, or pramiracetam; in addition to compounds that interact with $Ca^{2+}$ channels such as 4-aminopyridine or 3,4-diaminopyridine; or in addition to peptides that can have modulatory effects on acetylcholine release, such as somatostatin; in combination with a peripheral antimuscarinic agent (such as pirenzepine, N-methylatropine, N-butylscopolamine, propantheline, methantheline, glycopyrrolate, or tropenzilium) to counteract peripheral adverse effects that might be expected at high doses, such as salivation, diarrhea, gastric secretion or vomiting, or in combination with transdermal scopolamine such as Scopoderm® to counteract nausea and/or vomiting; in combination with antidepressants such as nortriptyline, amitriptyline, imipramine, minaprine in order to alleviate both the cognitive impairments and depressive symptoms associated sometimes with SDAT, AAMI, mixed SDAT/Parkinson's disease (PD); in combination with M2-antimuscarinic drugs such as secoverine, AFDX-116 (c. f. Hammer et al, 1986 Life Sci. 38:1653) in order to counteract peripheral adverse side effects that might be expected at high doses of the compounds, to counteract inhibitory effects of such agonists at central inhibitory presynaptic and postsynaptic receptors of M2 type and to potentiate the release of acetylcholine via inhibition of inhibitory autoreceptors of M2 type at intact terminals; in combination with nicotinic agonists such as nicotine in order to stimulate both the nicotinic and muscarinic receptors in the brain; in combination with an adrenergic agonist (clonidine or quanfamicine) in order to alleviate both the cognitive and other impairments associated with a mixed cholinergic-noradrenergic deficiency in SDAT; in combination with inhibitors of neuronal serotonin reuptake such as alaproclate, zimelidine in order to alleviate both the cognitive and other emotional functions in SDAT; in combination with monoamine oxidase-B inhibitors like deprenyl in order to alleviate both cognitive and other motor impairments associated with mixed states such as SDAT/PD; in combination with Nerve Growth Factor (NGF, which is administered either by a nasal spray or intracerebroventricularly).

The spiro-compounds of the present invention, with or without the aforementioned additional active substances, can be administered for example, by way of injection in a suitable diluent or carrier, per os, rectally in the form of suppositories, by way of insufflation or nasal spray, by infusion or transdermally in a suitable vehicle with or without physostigmine or tetrahydroaminoacridine.

The present spiro-compounds may also be of potential use for the treatment of disorders requiring the application of a long-lasting cholinergic agent of mild local activity. Such an agent is needed in disorders such as glaucoma, as the compound is not destroyed by the enzyme which deactivates acetylcholine, i.e. acetyl— and butyryl-cholinesterase, and may also be used for the treatment of peripheral cholinergic disorders such as myasthenia gravis, urinary bladder dysfunctions, Adi's disease and Eaton-Lambert disease. These compounds might also be used in disturbances where cholinergic underactivity is induced by drugs.

Where the present spiro-compounds are anticholinergic agents (which may readily determined by the skilled person) they may potentially be used fop treatment of disorders due to a cholinergic hyperfunction, whether this be spontaneous or drug-induced. Moreover, the present compounds are of potential use in the treatment of various diseases such as PD, pseudo-PD, mixed AD/PD, primary dystonias, spasmodic torticollis, cranial dystonia, depression, motion sickness, akathisia (after neuroleptic withdrawal), central hypertension, human head injury, mixed tardive dyskinesia and PD, manic-depression, as adjuncts in surgery instead of atropine, scopolamine, etc., in intoxication due to an excess of acetylcholine like inhibition of acetylcholinesterase. These may also be used in ophthalmology when either prolonged or short-term mydriasis is required.

The present spiro-compounds may also potentially be used in the treatment of disease characterized by excess peripheral-like activity such as asthma, chronic obstructive pulmonary disease, peptic ulcer disease. For these peripheral disorders it is particularly recommended to use quaternary salts of the present compounds.

Quaternary ammonium salts are widely used in therapy at the present time. Thus, examples of quaternary cholinergic agonists are acetylcholine chloride, bethanechol chloride and carbachol (see e.g. Goodman & Gilman's "The Pharmacological Basis of Therapeutics", Seventh Edition, Macmillan Publishing Co., 1985, at page 104). Quaternary anticholinesterase agents are, for example, neostigmine bromide, ambenonium chloride, pyridostigmine bromide, edrophonium chloride, demecarium bromide, and echothiphate iodide; pralidoxime chloride is used as a cholinesterase reactivator (see Goodman & Gilman, loc cit, at pages 122–123).

Quaternary derivatives of belladonna alkaloids, e.g. methscopolamine bromide and homatropine methylbromide, as well as certain synthetic quaternary compounds, e.g. methantheline bromide, and propantheline bromide, are used in the treatment of gastrointestinal disorders (see Goodman & Gilman, loc cit, at pages 139–140).

In "Medicinal Chemistry" by Alfred Burger, Second Edition, Interscience Publishers, 1960, at page 497, there is mentioned a prediction that quaternary ammonium ions, regardless of their chemical structure, produce curareform paralysis and the corroboration of this prediction in a later studies. This property of quaternary compounds is utilized in anesthesia, particularly as an adjuvant in surgical anesthesia to obtain relaxation of skeletal muscle, as described in Goodman & Gilman, loc cit, in Chapter 11 under the title of "Neuromuscular Blocking Agents", at pages 222–235.

This neuromuscular blocking activity of quaternary compounds, as discussed in Burger, loc cit, has not prevented the development and clinical application of quaternary compounds in therapeutics in the course of the ensuing 33 years. It would be evident to the skilled person that many factors influence the selection of any compound (including a quaternary compound) for application in clinical therapy, including effectiveness for the intended purpose, safety, possible side-effects and therapeutic index. Insofar as the present invention relates to "pharmaceutically acceptable quaternary compounds" which are structurally derived from compounds of the invention containing tertiary nitrogen atoms, the skilled addressee would well understand how to interpret this expression in the light of the relevant knowledge available in the art.

The invention will now be illustrated by the following non-limiting Examples.

EXAMPLE 1

1-Methylpiperidine-4-spiro-5'-(3'-ethylhydantoin) AF160 a) 1-Methylpiperidine-4-spiro-5'-hydantoin

A mixture of solutions of 1-methylpiperidine-4-one (36.44 g, 0.322 mole) in ethanol (150 ml), ammonium carbonate (93.0 g, 0.968 mole) in water (400 ml) and potassium cyanide (25.8 g, 0.396 mole) in water (82 ml) was heated at 60° C. for 2.5 hr., and then left at room temperature overnight. The precipitated 1-methylpiperidine-4-spiro-5'-hydantoin was filtered off and washed with small amounts of cold water, ethanol and ether to give a crystalline powder (27.0 g). Concentration of the filtrate and washings gave a second crop (20.0 g). The product was crystallized from methanol mp. 265–276 (dec.).

IR (KBr) 3170 (NH); 1700 (C=O) cm$^{-1}$. Mass Spectrum m/e 183($M^+$, 38%); 71 (100%) $^1$H-NMR ($D_2O$) 1.8 (2H); 2.06 (sextet, 2H); 2.49(s, —$CH_3$); 2.58 (t, 2H); 3.14 (t, 1H); 3.20 (t, 1H) ppm.

b) 4-Amino-1-methylpiperidine-4-carboxylic acid

1-Methylpiperidine-4-spiro-5'-hydantoin (9.75 g, 0.0533 mole) and barium hydroxide octahydrate (28.8 g, 0.0913 mole) in water (150 ml) were heated at 160° C. in a bomb for 3 hr. The content of four such batches were combined and the precipitated barium carbonate was filtered off. The filtrate was neutralized with solid $CO_2$ and the precipitate removed by filtration. The filtrate was concentrated to give 4-amino-1-methylpiperidine- 4-carboxylic acid (32.0 g., 95%) mp. 275°–280° C. (dec.).

IR (KBr) 3300, 1655, 1580 cm$^{-1}$ Mass Spectrum m/e 158 ($M^+$, 90%); 141 (98%, M—OH); 113 (12%, M—$CO_2H$); 96 (100%); 71 (52%). $^1$H-NMR ($C_5D_5N+D_2O$) 1.2 (m, 2H); 1.48 (s, $CH_3N$—); 1.7 (m, 2H); 1.9 (m, 2H); 2.0 (m, 2H) ppm.

c) 1-Methylpiperidine-4-spiro-5'-(3'-ethylhydantoin), AF160

To a mixture of 1-methylpiperidine-4-spiro-5'-hydantoin (5 g, 27 mmole) and potassium hydroxide (2.08 g, 37 mmole) in 100 ml absolute ethanol ethyl bromide (15 g, 137 mmole) was added. The mixture was heated at 80° C. and samples were taken in 0.5 hr intervals and checked by GLC relative to internal standard (diphenylmethane).

The basicity was monitored by titration (HCl 1N) followed by addition of potassium hydroxide (total of 2.1 g). After obtaining the maximum yield (2.5 hrs), the solution was evaporated, water (50 ml) was added and the aqueous solution was extracted with chloroform and chromatographed on silica gel column using chloroform/methanol/aqueous ammonia (80:20:1) as an eluting system. The product was dissolved in ether and precipitated as a hydrochloric acid salt by addition of HCl in isopropanol m.p. 278–280° C.

Mass spectrum m/e 211($M^+$, 45%); 71 (100%).

$^1$H-NMR (free base, $CDCl_3$). 1.2(t,J=6 Hz, 3H); 1.6–1.7(m, 2H); 1.9–1.95(m,2H); 2.1–2.2(m,2H); 2.34(S,3H); 2.85–2.95(m,2H); 3.5(q, J=6 Hz,2H); $^1$H-NMR (HCl salt, $D_2O$ ) 1.1(t,J=6 Hz,3H); 1.95–2.05(m,2H); 2.2–2.3(m,2H); 2.85(S,3H); 3.0–3.2(m,2H); 3.4–3.5(m,2H); 3.5(q, J=6 Hz, 2H) ppm. $^{13}$C-NMR (free base, $CDCl_3$) 14.0; 33.0; 33.1; 46.0; 52.8; 59.9; 157.0; 177.0 ppm.

UV (free base, $H_2O$ ) lambda$_{max}$ 208nm ($\epsilon$ 3500).

EXAMPLE 2

1-methylpiperidine-4-spiro-5'-(1'-acetylhydantoin) AF164 a) AF164A

A mixture of 1-methylpiperidine-4-spiro-5'-hydantoin (3.25 g) in acetic anhydride (50 ml) was heated under reflux for 3 hr. The excess reagent was removed at reduced pressure to leave a solid which was dispersed in ether and filtered to give a white solid (3.75 g) crystallized from methanol-dichloromethane m.p. 250°–254° C. (dec.) AF164A.

$^1$H-NMR ($D_2O$) 1.89(m,2H); 2.44(s,$CH_3CO$—); 2.86(s, $CH_3N$—). 2.98(m,2H); 3.41 (m,2H); 3.67(m,2H) ppm.

$^{13}$C-NMR (D$_2$O, dioxane as internal standard) 26.6 (C$_3$ & C$_5$); 26.9 (CH$_3$CO—); 43.8(CH$_3$N—); 51.4(C$_2$ & C$_6$); 62.0 (C$_4$); 67.3 (dioxane); 166.0 (C$_2$·); 173.8 (CH$_3$CO—); 189.2 (C$_4$·) ppm. MS m/e 225 (M$^+$); 210; 166; 155; 123; 95; 71 (100%); 70.

b) AF164B

Part of AF164A (1.10 g) was made basic with saturated aqueous Na$_2$CO$_3$ solution and extracted with a mixture of methanol-dichloromethane, the extract was evaporated and the residue extracted again with the same solvent mixture, the extract filtered and the filtrate evaporated, the residue (1.0 g) was triturated with acetone giving a white solid which was crystallized from CH$_2$Cl$_2$—CH$_3$OH—CH$_3$CN m.p. 225°–230° C. (dec.) AF164B.

$^1$H-NMR (D$_2$O) 1.53(m,2H); 2.21(s,CH$_3$CO—); 2.39(s, CH$_3$N—); 2.65–2.80 (m, 6H) ppm.

$^{13}$C-NMR (D$_2$O, with dioxane as internal standard) 26.9 (CH$_3$CO—); 28.3 (C$_3$ & C$_5$); 45.0 (CH$_3$N—); 50.9 (C$_2$ & C$_6$); 64.9 (C$_4$); 67.3 (dioxane); 168.8 (C$_2$·); 173.6 (CH$_3$CO—); 193.9 (C$_4$·) ppm.

MS m/e 225 (M$^+$); 183 (M$^+$—CH$_2$=C=O); 166; 154; 123; 95; 71 (100%).

c) AF164 (HCl salt)

An HCl salt of AF164 was prepared by treating a solution of AF164A or AF164B in methanol with HCl dissolved in isopropanol till the pH was acidic (pH 1–2). The salt, AF164 (HCl salt), precipitated after a short time as a white solid m.p. 301°–2° C. (dec.).

$^1$H-NMR (D$_2$O) 2.17 (m, 2H); 2.50 (s, CH$_3$CO—); 2.93 (s, CH$_3$N—); 3.10 (m, 2H); 3.48–3.71 (m, 4H) ppm.

$^{13}$C-NMR (D$_2$O, dioxane as internal standard) 26.7 (C$_3$ & C$_5$); 26.9 (CH$_3$CO—); 43.9 (CH$_3$N—); 51.1 (C$_2$ & C$_6$); 61.8 (C$_4$); 67.3 (dioxane); 154.8 (C$_2$·); 173.4 (CH$_3$CO—); 176.0 (C$_4$·) ppm.

Hydrolysis of AF164

AF164A and AF164B are hydrolyzed by reflux in 0.2N aqueous NaOH (1–2 hr.) to give 1-methylpiperidine-4-spiro-5'-hydantoin, identified by comparison of its TLC and $^1$H-NMR to an authentic sample.

EXAMPLE 3

Piperidine-4-spiro-5'-(3'-ethylhydantoin) AF160(Des)

To a solution of dried AF160 (2.0 g, 9.5 mmole) in dichloroethane (25 ml., dried over molecular sieves) α-chloroethyl chloroformate (1.0 ml., 9.3 mmole) was added at room temperature and the mixture was heated to 60° C. for 1 h. Dichloroethane was removed in vacuo, the solid obtained was dissolved in 20 ml methanol and the solution was heated for another 30 minutes at 60° C. Then methanol was removed in vacuo and the oily solid obtained was dissolved in aqueous sodium carbonate and washed with ether. The aqueous layer was extracted with chloroform and the extract evaporated to yield a crude oil which was further purified by column chromatography on a silica gel column. Elution with chloroform: methanol: aqueous ammonia (4:1:0.1) gave AF160(Des) (1.12 g., 60% yield) as a white powder m.p. 225°–227° C.

MS m/e 197 (M$^+$base peak); 57

$^1$H-NMR (CDCl$_3$) 1.17 (t, J=6 Hz, 3H); 1.65–1.7 (m,2H); 1.85–2.0(m,2H); 2.75–2.85(m,2H); 3.05–3.15(m,2H); 3.5(q,J=6 Hz, 2H) ppm.

EXAMPLE 4

1-Methylpiperidine-4-spiro-5'-(3'-methylhydantoin), AF178

To a mixture of 1-methylpiperidine-4-spiro-5'-hydantoin (5.0 g., 27.3 mmole) and sodium hydroxide (2.0 g., 50 mmole) in 120 ml methanol, methyl tosylate (11.2 g., 60 mmole) was added. The reaction mixture was stirred overnight at room temperature, methanol was removed by evaporation and the oily residue was dissolved in aqueous potassium carbonate and extracted with chloroform. The organic extract was evaporated and the crude product obtained was further purified by column chromatography on silica using chloroform: methanol: aqueous ammonia (9:1:0.1) as an eluting system to yield 1.2 g. 22% of a white solid m.p. 229°–231° C.

MS m/e 197 (M$^{+, 30\%}$); 71 (100%).

$^1$H-NMR (free base, CDCl$_3$) 1.6–1.7(m,2H); 2.1–2.3(m, 4H); 2.34(s,3H); 2.85–2.95 (m,2H); 3.02(s,3H) ppm.

EXAMPLE 5

Piperidine-4-spiro-5'-(3-methylhydantoin) AF179

The white powdery product which was obtained in the same manner as in Example 3, was dissolved in isopropanol and acidified using hydrochloric acid to yield a white precipitate. m.p. above 320° C. (dec.).

MS m/e 183(M$^+$, base peak); 57.

$^1$H-NMR(HCl salt, D$_2$O); 2.0(m,2H); 2.2(m,2H); 2.96(s, 3H); 3.3 (m,2H); 3.6 (m,2H).

EXAMPLE 6

1-Methyl Piperidine-4-spiro-5'-(3'-propargylhydantoin) AF185

The white powdery product which was obtained in the same manner as in Example 1, m.p. 172°–174° C.

MS m/e 221 (M$^+$, base peak); 149; 196.

$^1$H-NMR (CDCl$_3$, free base) 1.61.85 (m, 2H); 2.22.25 (m,4H); 2.28 (t,J=2.4 Hz, 1H); 2.4 (s, 3H); 2.95 (m, 2H); 4.3 (d, J=2.4 Hz, 2H); 6.4 (bs, 1H) ppm.

EXAMPLE 7

1-Methylpiperidine-4-spiro-4'-(2', 5'-bis(methylthio)-4'H-imidazole) AF177

To a solution of 1-methylpiperidine-4-spiro-5'-(2',4'-dithiohydantoin) (1.00 g., 4.65 mmole; see Example 11) in methanol (15 ml) sodium hydroxide (0.30 g., 7.50 mmole) and then gradually a solution of methyl iodide (1.00 g., 7.04 mmole) in methanol (3.0 ml.) were added. The reaction mixture was stirred at room temperature for 1.5 h. The resulting precipitate (NaBr) was filtered and washed with methanol. The filtrate and washings were combined and the solvent removed. The residue left after removal of the solvent was made basic with aqueous potassium carbonate and then extracted with ether. The organic extract was dried (Na$_2$SO$_4$) and the solvent removed to leave a residue which was chromatographed on a column of silica gel. Elution with a solvent mixture of ether: chloroform: methanol: ammonium hydroxide (aq.) 78:18:3:1 gave the title compound AF177 crystallized from hexane mp 101°–102° C. (465 mg).

$^1$H-NMR (CDCl$_3$) 1.33 (m, 2H); 1.98 (m, 2H); 2.39 (s, CH$_3$N—); 2.56 (s, CH$_3$S—); 2.59 (s, CH$_3$S—); 2.48–2.64 (m, 2H); 2.82 (m, 2H) ppm.

$^{13}$C-NMR (CDCl$_3$) 14.1 (CH$_3$ S—); 14.2 (CH$_3$ S—); 34.9 (C$_3$ & C$_5$); 46.1 (CH$_3$ N—); 52.2 (C$_2$ & C$_6$); 83.0 (C$_4$); 171.6 (C$_2$·); 203.5 (C$_5$·) ppm.

MS m/e 244 (M$^+$+1); 185; 149; 93; 75

IR (KBr) 2920; 2797; 1535; 1477; 1465; 1452; 1378; 1316; 1286; 1210; 1108; 1054; 1000; 965; 942; 900; 776; 696 cm$^{-1}$.
UV (EtOH) lambda$_{max.}$ 257 nm ($\epsilon$ 16100).

EXAMPLE 8

1-Methylpiperidine-4-spiro-5'-(3'-ethyl-4'-thiohydantoin) AF182

A sample of 1-methylpiperidine-4-spiro-4'-(1'-ethyl-2'-ethylthio-2-imidazoline-5'-thione) AF170 (100 mg; see Example 12) was dissolved in 20% HCl (1 ml.) and the solution refluxed for 1.5 h. The reaction mixture was made basic with conc. solution of NaOH to pH14 and then extracted with dichloromethane. The organic extract was dried (Na$_2$SO$_4$) and the solvent evaporated to give 1-methylpiperidine-4-spiro-5'-(3'-ethyl-4'-thiohydantoin) as a white solid (74 mg) crystallized from petroleum ether-dichloromethane m.p. 176°–178° C.

$^1$H-NMR (CDCl$_3$) 1.25 (t, J=7.2 Hz, C$\underline{H}_3$CH$_2$—); 1.54 (m, 2H); 2.10 (m, 2H); 2.36 (s, CH$_3$ N—); 2.41 (m, 2H); 2.96 (m, 2H); 3.94 (q, J=7.2 Hz, —C$\underline{H}_2$CH$_3$); 7.23 (NH) ppm.
$^{13}$C-NMR (CDCl$_3$) 11.8 (C$\underline{H}_3$CH$_2$—); 36.9 (C$_3$ & C$_5$); 37.4 (—C$\underline{H}_2$CH$_3$); 46.1 (CH$_3$N—); 51.2 (C$_2$ & C$_6$); 68.1 (C$_4$); 157.1 (C$_{2'}$); 208.1 (C$_{4'}$) ppm.
MS m/e 227 (M$^+$); 211 (M$^+$—O); 194 (M$^+$—SH); 170 (M$^+$—C$_3$H$_7$N); 71; 70 (100%).
UV (EtOH) lambda$_{max.}$ 280 nm ($\epsilon$ 13600), 229 nm ($\epsilon$ 4400).

EXAMPLE 9

1-Methylpiperidine-4-spiro-5'-(4'-methylthio-3'-imidazoline-2'-thione) AF183

When repeating the reaction in Example 7 but using equivalent amounts of methyl iodide, sodium hydroxide and dithiohydantoin, there was obtained in addition to the bis-(methylthio) derivative AF177, 1-methylpiperidine- 4-spiro-5'-(4'-methylthio-3'-imidazoline-2'-thione) AF183. m.p. 218°–220° C. (dec.) (from dichloromethane-acetone).
$^1$H-NMR (CDCl$_3$) 1.74 (m, 2H); 2.07 (m, 2H); 2.37 (m, 2H); 2.39 (s, CH$_3$N—); 2.69 (s, CH$_3$S—); 2.95 (m, 2H); 10.3 (brs. —NH—) ppm.
MS m/e 229 (M$^+$); 182 (M$^+$—CH$_3$S); 123; 122; 70.
UV (EtOH) lambda$_{max.}$ 312 nm ($\epsilon$ 12000), 280 nm ($\epsilon$ 15300).

EXAMPLE 10

1-Methylpiperidine-4-spiro-5'-(3'-ethyl-2',4'-dithiohydantoin) AF163.

Powders of 1-methylpiperidine-4-spiro-5'-(3'-ethylhydantoin) (0.570 g). and phosphorus pentasulfide (0.570 g), were intimately mixed and refluxed in tetraline (15ml) for 2hr. After allowing the reaction mixture to cool to room temperature, a brown hard precipitate had formed; the tetraline was removed under reduced pressure and the precipitate was disintegrated and washed with petroleum ether. It was made basic with a concentrated aqueous NaOH solution and extracted with dichloromethane. The extract was dried (Na$_2$SO$_4$) and evaporated to give a residue (0.250 g.) which was chromatographed on a column of silica gel (Merck) (60.15 g.). Elution with a solvent mixture of chloroform;ether;methanol;ammonium hydroxide 77:18:4:1, gave a pure product AF163(50mg),crystallized from dichloromethane-ether m.p. 223°–225° C.(dec.).
$^1$H-NMR (CDCl$_3$) 1.27(t,J=7.2 Hz; C$\underline{H}_3$CH$_2$—);1.55–1.67(m;2H);2.03–2.19(m,2H); 2.26–2.46(m,2H); 2.36(s,CH$_3$N—); 2.89–3.04(m,2H); 4.27(q,J=7.2 Hz; —C$\underline{H}_2$CH$_3$); 8.25(brs.—NH—) ppm.
$^{13}$C-NMR (DMSO-d$_6$) 11.6 (C$\underline{H}_3$CH$_2$—); 36.9(C$_3$&C$_5$); 39.9(—C$\underline{H}_2$CH$_3$);45.9(CH$_3$N);49.9(C$_2$&C$_6$);72.9(C$_4$);179.8(C$_{2'}$); 207.8(C$_{4'}$) ppm.
MS m/e 243(M$^+$); 186(M$^+$—$^C$$_3$H$_7$N); 149; 71; 70(100%); 57.
IR (KBr) 3177(NH); 2930; 2778; 1513; 1434;1357; 1231; 1116; 1090; 1070; 1040; 961; 801; 780; 626; 546; 457 cm$^{-1}$.
UV (EtOH) lambda$_{max.\ 302}$ nm. ($\epsilon$ 34200), 226 nm. ($\epsilon$ 7700).
Synthesis of the tartrate salt of AF163
To a solution of AF163 free base (0.735 g., 3.025 mmole) in methylene chloride (15ml)—methanol (5ml.) a solution of L(+) tartaric acid (0.214 g., 1,427 mmole) in methanol (2.0 ml.) was added. The mixture was stirred at room temperature for 0.5 hr., then the solvents were evaporated and the residue was suspended in ether-methylene chloride, filtered and washed with the same solvent mixture to give a yellow solid AF163(tartrate) m.p. 221°–225° C. (dec.; 0.923 g., 96% yield).
$^1$H-NMR (D$_2$O) 1.27 (t,J=7.2 Hz, C$\underline{H}_3$CH$_2$—); 2.08 (m,2H); 2.49(m,2H); 3.01 (s,CH$_3$N—); 3.31 (m,2H); 3.76 (m,2H); 4.26 (q,J=7.2 Hz,—C$\underline{H}_2$CH$_3$); 4.37 (s,—C$\underline{H}$OH) ppm.

EXAMPLE 11

1-methylpiperidine-4-spiro-5'-(2',4'-dithiohydantoin) AF173.

A solution of 1-methyl-4-piperidone (29.35 g., 0.260 mole), potassium cyanide (26.57 g., 0,408 mole), ammonium chloride (21.00 g., 0.393mole) and carbon disulfide (26 ml.) in ethanol (200 ml.)-water (50 ml.) was heated under reflux (50°–55° C.) for 8 hr. The reaction mixture was left at room temperature overnight and the precipitate obtained was filtered and washed with water and then with ethanol to give a yellow solid (26.3 g.;47.0% yield) m.p.250°–253° C. (dec.), crystallized from methanol m.p.252°–254° C. (dec.).
$^1$H-NMR (DMSO-d$_6$) 1.43–1.56(m,2H); 1.89–2.05(m,2H); 2.21(s,CH$_3$N—); 2.26–2.40(m,2H); 2.64–2.79(m,2H); 11.14(br.s.,—NH—) ppm.
$^{13}$C-NMR (DMSO-d$_6$) 36.2(C$_3$&C$_5$); 45.5(CH$_3$N—); 49.9(C$_2$&C$_6$); 74.8(C$_4$); 81.5(C$_{2'}$); 212.0(C$_{4'}$) ppm.
MS m/e 215(M$^+$); 183(M$^+$—S); 182(M$^+$—SH); 181; 158(M$^+$—$^C$$_3$H$_7$N); 123; 102; 77; 71; 70(100%).
IR (KBr) 3130 (NH); 1484; 1449; 1350; 1295; 1231; 1198; 1176; 1145; 083; 1062; 957; 721; 545; 504 cm$^{-1}$. UV (0.01N HCl) lambda$_{max.}$ 298 nm. ($\epsilon$ 32000), 220 nm. ($\epsilon$ 8000).

EXAMPLE 12

1-methylpiperidine-4-spiro-5'-(3'-ethyl-2',4'-dithiohydantoin) AF163;
1-methylpiperidine-4-spiro-5'-(4'-ethylthio-3'-imidazoline-2'-thione) AF176;
1-methylpiperidine-4-spiro-4'-(1'-ethyl-2'-ethylthio-2'-imidazoline-5'-thione) AF170.
To a suspension of 1-methylpiperidine-4-spiro-5'-(2',4'-dithio-hydantoin) AF173 (3.30 g.; 15.3 mmole) in dry DMF (30 ml.) NaH (0.760 g. 60% in mineral oil; 19.0 mmole) was added and the mixture stirred at 50° C. for 1.5 hr. A solution of EtBr (1.85 g.; 17.0 mmole) in DMF (6 ml.) was gradually added to the above mixture and it was stirred at 75°–80° C. for 4 hr. After standing at room temperature overnight, the precipitate formed (NaBr) was filtered and washed with ether. The filtrate and washings were combined and evaporated to give an oil from which a dichloromethane insoluble solid (1.5 g.) was separated, which was found to be starting material (identical NMR and TLC). The residue was chromatographed on a column of silica gel. Elution with a solvent mixture of: ether; chloroform: methanol: ammonia (aq.) 68:27:4:1 gave first 1-methylpiperidine-4-spiro-5'-(3'-ethyl-2',4'-dithiohydantoin) AF163 (0.95 g.), identical to the product obtained before from the reaction of AF160 with phosphorus pentasulfide. The elution was continued to give 1-methylpiperidine-4 -spiro-5'-(4'-ethylthio-3'-imidazoline-2'-thione) AF176 (0.15 g.). Crystallized from hexane-dichloromethane m.p. 212°–215° C. (dec.).

$^1$H-NMR (CDCl$_3$) 1.42 (t, J=7.2 Hz, C$\underline{H}_3$CH$_2$—); 1.73 (m,2H); 2.06 (m,2H); 2.31 (m,2H); 2.38 (s, CH$_3$N—); 2.95 (m,2H); 3.33 (q, J=7.2 Hz, —C$\underline{H}_2$CH$_3$); 10.0 (br. —NH—) ppm.

$^{13}$C-NMR (DMSO-d$_6$) 14.2 (C$\underline{H}_3$CH$_2$—); 25.6 (—C$\underline{H}_2$CH$_3$); 35.0 (C$_3$&C$_5$); 45.8 (CH$_3$N—); 50.5 (C$_2$&C$_6$); 74.3 (C$_4$); 192.1 (C$_{2'}$) 198.1 (C$_{4'}$) ppm.

MS m/e 243 (M$^+$); 182 (M$^+$—EtS,100%); 156(M$^+$—EtSCN); 123; 124; 96; 71; 70; 57.

IR (KBr) 3135 (NH); 2930; 2788; 1476;1463; 1446; 1281;1257; 1232; 1158; 1141; 1121; 1096; 958; 711; 674; 535 cm$^{-1}$.

UV (EtOH) lambda$_{max.}$ 314 nm. ($\epsilon$5400) inf., 282 nm. ($\epsilon$6700).

Repeating the above reaction with 1.5 molar excess of EtBr over AF173 gave in addition to the above-stated monoethyl derivatives, the diethyl derivative 1-methylpiperidine-4-spiro-4'-(1'-ethyl-2'-ethylthio-2'-imidazoline-5'-thione) AF170 m.p.66°–67° C. (crystallized from hexane).

$^1$H-NMR (CDCl$_3$) 1.24 (t, J=7.2 Hz, C$\underline{H}_3$CH$_2$—); 1.24 (m,2H); 1.44 (t, J=7.2 Hz, C$\underline{H}_3$CH$_2$—); 2.27 (m,2H); 2.39 (s, CH$_3$N—); 2.52 (m,2H); 2.81 (m,2H); 3.24 (q, J=7.2 Hz, —C$\underline{H}_2$CH$_3$); 3.93 (q, J=7.2 Hz, —C$\underline{H}_2$CH$_3$) ppm.

$^{13}$C-NMR (CDCl$_3$) 12.2 (C$\underline{H}_3$CH$_2$—); 13.9 (C$\underline{H}_3$CH$_2$—); 25.7 (—C$\underline{H}_2$CH$_3$); 36.8 (C$_3$&C$_5$); 39.0 (—C$\underline{H}_2$CH$_3$); 46.1 (CH$_3$N—); 51.5 (C$_2$&C$_6$); 82.2 (C$_4$); 158.5 (C$_{2'}$); 216.7 (C$_{5'}$) ppm.

MS m/e 271(M$^+$); 242(M$^+$-Et); 214(M$^+$—C$_3$H$_7$N); 185; 162; 75; 71; 70(100%); 57.

IR (KBr) 1574 (C=N); 1446; 1372; 1354; 1212; 1071; 1060;936 cm$^{-1}$.

UV (EtOH) $_{max.}$($\epsilon$) 296(22000); 252(17700) nm.

Acid hydrolysis of AF176.

To AF176 (48 mg.), aq. HCl (1 ml.,20%) was added. An immediate odor of a mercaptan was noticed. The solution obtained was stirred at room temp. for 1 hr. then evaporated at 50° C. under reduced pressure, giving as a white solid 1-methylpiperidine-4-spiro-5'-(2'-thiohydantoin) HCl salt (X).

$^1$H-NMR (D$_2$O) 2.10–2.43 (m,4H); 2.94 (s,CH$_3$N—); 3.20 (m,1H); 3.47–3.78 (m,3H) ppm.

MS m/e 199 (M$^+$); 181; 171 (M$^+$—CO); 156 (M$^+$—HNCO); 142 (M$^+$—C$_3$H$_7$N); 111; 96; 71; 70; 57.

UV (H$_2$O) lambda$_{max.}$ 264 nm. ($\epsilon$20400), 224 nm. ($\epsilon$8600).

EXAMPLE 13

1-methylpiperidine-4-spiro-5'-(2'-thiohydantoin).

A solution of 1-methylpiperidine-4-spiro-5'-(2',4'-dithiohydantoin) AF173 (10.0 g.) in ethanolamine (40 ml.) - water (75 ml.) was refluxed for 1.75 hr. The solvent and excess reagent were removed under reduced pressure. Repeated crystallization of the residue from acetonitrile/dichloromethane, acetone, and ethanol-acetonitrile gave pure 1 -methylpiperidine-4-spiro-5'-(2'-thio-4'-β-hydroxyethyliminohydantoin) m.p. 230°–231° C. (dec.).

$^1$H-NMR (D$_2$O) 1.74 (m, 2H); 1.94 (m, 2H); 2.26 (s, CH$_3$N—); 2.17–2.34 (m, 2H); 2.92 (m, 2H); 3.54 (t, J=5.4 Hz, —C$\underline{H}_2$OH); 3.74 (t, J=5.4 Hz, =NCH$_2$—) ppm.

$^{13}$C-NMR (DMSO-d$_6$) 33.7 (C$_3$ & C$_5$); 45.4 (—CH$_2$—) 45.9 (CH$_3$N—); 50.6 (C$_2$ & C$_6$); 59.2 (—CH$_2$—); 66.3 (C$_4$); 182.5 (—C=S); 195.0 (—C=N—) ppm.

MS m/e 242 (M$^+$); 224 (M$^+$—H$_2$O); 199; 185; 172 (M$^+$-70); 154 (M$^+$-70-H$_2$O); 71; 70.

UV (0.01N HCl) lambda$_{max.}$ 227 nm. ($\epsilon$22200), 242 nm. ($\epsilon$10200).

The iminohydantoin derivative (1.40 g.) was dissolved in aqueous HCl (5.0 ml., 1:1) and refluxed for 1 hr. The reaction mixture was evaporated under reduced pressure and the residue crystallized from methanol to give 1-methylpiperidine-4-spiro-5'-(2'-thiohydantoin) hydrochloride (0.756 g.), identical to the product obtained from the hydrolysis of AF176.

EXAMPLE 14

1-Methylpiperidine-4-spiro-5'-(oxazolidine-2'-thione) AF165

To anhydrous DMSO (10 ml) containing a small amount of KOH powder, 4-aminomethyl-4-hydroxy-1-methylpiperidine (0.595 g., 4.13 mmole) was added with stirring, followed by carbon disulfide (0.340 g., 4.47 mmole). The reaction mixture was heated at 50° C. for 2 h. The solvent was removed in vacuum and the residue was crystallized several times from methanol, acetone and dichloromethane to give a crystalline solid m.p. 190°–195° C. (211 mg).

$^1$H-NMR (CDCl$_3$) 1.80–1.98 (m, 2H); 2.03–2.16 (m, 2H); 2.32 (S, CH$_3$N—); 2.44–2.72 (m, 4H); 3.51 (s-C$\underline{H}_2$N-C=S) ppm.

$^{13}$C-NMR (DMSO-dc) 35.1 (C$_3$Cl$_5$); 45.7 (CH$_3$N—); 51.5 (C$_2$Cl C$_6$); 53.1 (—CH$_2$NH—); 86.4 (C$_4$); 187.2 (—C=S) ppm.

EXAMPLE 15

N-methylnortropane-3-spiro-5'-(3'-methylhydantoin) AF167, and
N-methylnortropane-3-spiro-5'-(3'-ethylhydantoin), AF168.

a) N-methylnortropane-3-spiro-5'-hydantoin

A mixture of tropinone (45 g, 0.32 mole) in ethanol (160 ml), ammonium carbonate (93 g, 0.96 mole) in water (400 ml), and potassium cyanide (25.8 g, 0.40 mole) in water (84 ml), was heated at 60° C. for 2 hours, and then kept at room temperature for 16 hours. N-methylnortropane-3-spiro-5'-hydantoin (61.33 g, 0.29 mole, 92% yield) separated and was dried in a dessicator: m.p. 330° C. Mass Spectrum m/e 209 (M$^+$)

$^1$H-NMR (CD$_3$COOD) 2.1(m,2H,H6=H7($\alpha$)), 2.3(m,2H, H2=H4($\beta$)), 2.4 (m, 2H, H2=H4($\alpha$)), 2.7 (m, 2H, H6=H7($\beta$)), 2.9 (s, 3H), 3.0 (bs, NH) 4.1 (bs, 2H, H1=H5) ppm.

$^1$H-NMR (DCl, D$_2$O) 2.3 (m, 4H, H6=H7($\alpha$) and H2=H4($\beta$)), 2.5 (m, 2H, H2=H4($\alpha$)), 2.7 (m,2H,H6=H7($\beta$)), 2.9(s,3H), 4.15(bs,2H,H1=H5)ppm.

$^{13}$C-NMR (DCl, D$_2$O) 25.5 (C6=C7, t), 33.5 (C2=C4, t), 39.7 (CH$_3$, q), 59.3 (C3-C5', s), 63.0 (C1=C5, d), 159.3 (C2', s), 180.2 (C4',s) ppm.

b) AF167 end AF168

N-methylnortropane-3-spiro-5'-hydantoin (1 eq.) and KOH (1 eq.) were mixed in water at room temperature for a few minutes. Methyl iodide or ethyl bromide (2 eq.) in methanol or ethanol was added dropwise to the aqueous solution. The reaction mixture was extracted with chloroform and dried over magnesium sulfate before evaporation. The products AF167 and AF168 were obtained in about 10% yield.

AF167

$^1$H-NMR (D$_2$O) 1.65 (m, 2H, H6=H7($\alpha$)), 1.8 (m, 2H, H2=H4($\beta$)), 2.2 (m, 2H, H2=H4($\alpha$)), 2.4 (m, 2H, H6=H7($\beta$)), 2.55 (s, 3H), 2.85 (s, 3H), 3.25 (bs, 2H,H1=H5) ppm.

$^1$H-NMR (CDCl$_3$ 1.55 (m, 2H, H6=H7($\alpha$)), 1.75 (m, 2H, H2=H4($\beta$)), 2.2 (m, 2H H2=H4($\alpha$)), 2.4 (s,3H), 2.45 (m, 2H, H6=H6($\beta$)), 3.0 (s,CH3), 3.3 (bs, 2H H1=H5), 6.3 (bs,NH) ppm.

Mass Spectrum m/e 223 (M$^+$)

AF168

$^1$H-NMR (CDCl$_3$, CD$_3$OD) 1.1(t, 3H), 1.6 (m, 2H, H6=H7($\alpha$)), 1.75 (m, 2H, H2=H4($\beta$)), 2.2(m, 2H,H2=H4($\alpha$)), 2.35(s,3H), 2.4(m, 2H, H6=H7($\beta$)), 3.3(bs,2H,H1=H5), 3.55(q,2H) ppm.

$^1$H-NMR (CDCl$_3$) 1.2 (t, 3H), 1.6 (m, 2H H6=H7($\alpha$)), 1.75 (m, 2H, H2=H4($\beta$)), 2.2 (m, 2H, H2=H4($\alpha$)), 2.4 (s,3H), 2.45 (m, 2H, H6=H7($\beta$)), 3.3 (bs, 2H, H1=H5), 3.55 (q, 2H), 6.3 (bs,NH) ppm.

$^{13}$C-NMR (CDCl$_3$, $\delta$) 13(CH$_3$CH$_2$), 25(C6=C7), 35(C2=C4), 40(N—CH$_3$), 40.5(N—CH$_2$), 59(C3-C5'), 60(C1=C5), 159(C2'), 180(C4') ppm.

Mass Spectrum m/e 237 (M$^+$)

EXAMPLE 16

1-methylpiperidine-4-spiro-5'-(3'-ethyloxazolidine-2'-one) AF172 a) 4-acetamidomethyl-4-hydroxy-1-methylpiperidine 4-aminomethyl-4-hydroxy-1-methylpiperidine (2.95 g, 0.02 mole), potassium carbonate (6.5 g, 0.047 mole) and acetic anhydride (8.5 g, 0.08 mole) in methanol were mixed at room temperature for two hours. Sodium hydroxide was added for neutralization and the solution extracted with chloroform. After evaporation, a yellow oil was obtained which was identified as 4-acetamidomethyl-4-hydroxy--1-methylpiperidine (3.4 g, 0.018 mole, 91% yield).

b) 4-ethylaminomethyl-4-hydroxy-1-methylpiperidine 4-acetamidomethyl-4-hydroxy-1-methylpiperidine (3.4 g, 0.018 mole) in dry THF was refluxed in the presence of lithium aluminium hydride (4 g). After 3 days, the mixture was poured into an ice-water bath and filtered through Celite. The solvent was evaporated and after addition of water the solution was extracted with chloroform, and the extract was dried with magnesium sulfate and evaporated to yield 1.03 g (33% yield) crude material. The product thus obtained, 4-ethylaminomethyl-4-hydroxy- 1-methylpiperidine, was used without further purification.

c) 1-methylpiperidine-4-spiro-5'-(3'-ethyloxazolidine-2-one) AF172

4-ethylaminomethyl-4-hydroxy-1-methylpiperidine (16.8 g, 0.1 mole) and N,N'-carbonyldiimidazole (32 g, 0.2 mole) were mixed in 400cc chloroform under nitrogen. Evaporation gave 50g crude material which was washed thoroughly with hexane, which after evaporation afforded the product, 1-methylpiperidine-4-spiro-5'-(3'-ethyloxazolidine-2-one) AF172, as a yellowish oil (16.8 g, 0.085 mole, 85% yield).

$^1$H-NMR (CDCl$_3$) $\delta$ 1.15(t,3H), 1.8(m,2H), 1.95(m,2H), 2.3(s,3H), 2.55(m,2H), 3.28(s,2H), 3.32(q,2H) ppm.

$^{13}$C-NMR (CDCl$_3$) 13(CH$_3$CH$_2$), 22(CH$_3$CH$_2$), 37(CH$_3$CH$_2$N), 39(CH$_2$NEt), 52(NCH$_2$CH$_2$), 55(C—O), 157.5 (C=O) ppm.

Mass spectrum m/e 198 (M$^+$)

EXAMPLE 17

1-methylpiperidine-4-spiro-4'-(3'-ethyloxazolidine-2-one) AF174 a) 4-acetamido-4-hydroxymethyl-1-methylpiperidine 4-amino-4-hydroxymethyl-1-methylpiperidine (2.95 g, 0.02 mole), potassium carbonate (6.5 g, 0.047 mole) and acetic anhydride (8.5 g, 0.08 mole) in methanol were mixed at room temperature for two hours. Sodium hydroxide was added for neutralization and the solution extracted with chloroform. After evaporation the white solid obtained was crystallized with warm acetone affording 4-acetamido-4-hydroxymethyl-1-methylpiperidine (1.67 g, 0.009 mole, 45% yield).

b) 4-ethylamino-4-hydroxymethyl-1-methylpiperidine 4-acetamido-4-hydroxymethyl-1-methylpiperidine (1.6 g, 8.6 mmoles) in dry THF was refluxed in the presence of lithium aluminium hydride (3 g). After 4 hours, the mixture was poured into an ice-water bath and filtered through Celite. The solvent was evaporated and after evaporation of most of the water, the solution was extracted with chloroform, dried with magnesium sulfate and evaporated to yield 1.13 g (77% yield) of quite pure material. AF167 The product, 4-ethylamino-4-hydroxymethyl-1-methylpiperidine, so obtained, was used without further purification.

c) 1-methylpiperidine-4-spiro-4'-(3'-ethyloxazolidine-2-one) AF174

4-ethylamino-4-hydroxymethyl-1-methylpiperidine (172 mg, 1 mmole) and N,N'-carbonyldiimidazole (486 mg, 3 mmoles) were mixed in chloroform under nitrogen during 3 hours. Following evaporation, a crude material was obtained which was washed thoroughly with hexane, which after evaporation afforded the product, 1-methylpiperidine-4-spiro-4'-(3'-ethyloxazolidine- 2-one) AF174, as a white solid (140 mg, 0.71 mmole, 71% yield).

$^1$H-NMR (CDCl$_3$) $\delta$ 1.10 (t,3H), 1.6(m,2H), 1.95(m,4H), 2.25(s,3H), 2.85(m,2H), 3.2(q,2H), 4.1(s,2H) ppm.

Mass spectrum m/e 198 (M$^+$)

EXAMPLE 18

2-N-Methylspiro-(1,3-succinimide 4,3')quinuclidine AF133 a) Ethyl (3-quinuclidylidene)-cyanoacetate

A mixture of 3-quinuclidinone (30 g., 0.2 mole), ethyl cyanoacetate (40 g., 0.35 mole), ammonium acetate (3.8 g.), acetic acid (11 g.) and 120 ml benzene, was heated under reflux and water was removed by azeotropic distillation (total of 4 ml water). The benzene solution was cooled, potassium carbonate (30 g.) in 120 ml water was added and the mixture was extracted with toluene (3×500 ml). The toluene extracts were combined, dried and the product was precipitated as a hydrochloric acid salt to yield 63 g. (95% yield) of crude product. TLC ammonium hydroxide (25% in water) 2% v/v in methanol on silica Art 5735 (Merck) R$_f$ 0.67. The product can be Further purified by crystallization in ethanol or isopropanol.

$^1$H-NMR$\delta$(CDCl$_3$-TMS) free base, :1.29(t,3H,CH$_3$); 4.2(q, 2H,CH$_2$);1.7–1.9, 2.8–3.2(m,quinuclidine skeleton).

$^{13}$C-NMR$\delta$(CDCl$_3$-TMS) : 14(CH$_3$); 62(CH$_2$O); 189(C=O); 162 (C=N); 115 (C—CN); 100 (C=C); 33.7 (C—H).

b) 3-carboethoxy-3-carboethoxymethylquinuclidine

Ethyl (3-quinuclidylidene)-cyanoacetate (64 g., 0.24 mole) and potassium cyanide (17 g., 0.26 mole) dissolved in 25 ml water, were dissolved in 125 ml ethanol. The mixture was refluxed For twenty minutes, cooled, decanted from potassium chloride and the remaining potassium chloride was washed with two 50 ml portions of ethanol. The combined alcoholic solution was evaporated and the oily residue was dissolved in 250 ml concentrated hydrochloride acid and refluxed for 24 hr. The solution was then evaporated and the residue washed several times with acetone and dried. The dried solid was refluxed in ethanol saturated with hydrogen chloride for 20 hr. Then ethanol was removed and the residue was basified carefully using sodium carbonate and extracted into chloroform. The chloroform solution was dried, evaporated and the crude diester was further purified by column chromatography using 2% methanol in chloroform as an eluting system.

MS m/e 2.69 ($M^+$); base peak m/e 196 (M-C-OEt).
$^1$H-NMR δ(CDCl$_3$-TMS) 1.2(dt, 6H, CH$_3$); 4.2–4.3 (dt, 4H), CH$_2$O); 1.3–1.6, 2.6–3.1 (m, quinuclidine skeleton).

c) 2-N-Methyl spiro-(1,3-succinimide 4,3') quinuclidine (AF133)

3-carboethoxy-3-carboethoxymethylquinuclidine (3.35 g, 12 mmole) was dissolved in 4.5 g methylamine and heated under pressure at 190° C. (90 hrs). The reaction mixture was cooled, evaporated and the solid residue was purified by column chromatography on silica using 2% methanol in chloroform containing 0.2 ammonia as an eluting system. AF133 was obtained as a white solid, m.p. 94°–96° C. 1.2 g (5.7 mmole).
MS $M^+$ 209.
$^1$H-NMR δ(CDCl$_3$-TMS). 3.4(d,1H)(H$_2$); 2.96(s,3H)(CH$_3$); 2.5(d,1H)(H$_2$); 1.5–1.9(m,quinuclidine skeleton).

EXAMPLE 19

2-N-Ethyl-spiro-(1,3-succinimide 4,3')quinuclidine
AF134

The crude 3-carboethoxy-3-carboethoxymethylquinuclidine (20 g.) was dissolved in 70% aqueous ethyl amine and heated at 140° C. under pressure for seven hrs. The reaction was monitored by G.C. The crude product was extracted with chloroform which was then dried and evaporated. The oily residue was purified by column chromatography on silica using chloroform/petroleum ether/ethanol/aqueous ammonia 17/13/3/0.4. The free base was precipitated as a hydrochloric acid salt, to yield 6.6 g. of white solid, m.p. 270°–272° C. TLC ammonium hydroxide (25% in water) 2% v/v in methanol on silica Art 5735 Merck R$_f$ 0.47.
MS $M^+$ 222
$^1$H-NMR δ(CDCl$_3$-TMS) free base: 1.5 (t,3H,CH$_3$); 3.5 (q,2H, N—CH$_2$); 1.6–3.3 (m,quinuclidine skeleton).

EXAMPLE 20

1-Methylpiperidine-4-spiro-5'-(oxazolidine-2',4'-dione) AF169 and 1-Methylpiperidine-4-spiro-5'-(3'-ethyloxazolidine- 2',4'-dione) AF180 a) 4-Hydroxy-4-cyano-1-methylpiperidine

To freshly distilled 1-methylpiperidin-4-one (81.72 g, 0.72 mole) in water (200 cc), were added about 100 cc HCl 37% to pH 3. The reaction mixture was cooled in an ice bath and potassium cyanide (49 g, 0.75 mole) in water (200 cc) was added at an adequate rate in order to maintain an internal temperature of about 10° C. The reaction was stirred two hours more after the addition and then filtered. After washing with water and drying, the product, 4-hydroxy-4-cyano-1-methylpiperidine, was obtained in 67% yield as a white powder (67 g, 0.48 mole, mp. 135° C.).
$^1$H-NMR (CDCl$_3$) δ 1.9 (m,2H), 2.2 (m,2H), 2.4 (s,3H), 2.45 (m,2H), 2.75 (m,2H), 2–3.5 (bm, 1H, OH) ppm.

b) 4-Hydroxy-4-carbamoyl-1-methylpiperidine

The compound 4-hydroxy-4-cyano-1-methylpiperidine (36.4 g, 0.26 mole) was gradually added to sulfuric acid (80 ml), under external cooling. The mixture was maintained at room temperature for 41 hours, then was added to powdered ice (30 g). The resulting solution was neutralized with barium carbonate (376 g) to pH 8–9 and after addition of water the resulting barium sulfate was separated and washed with methanol. The filtrate was concentrated under reduced pressure. The product, 4-hydroxy-4 -carbamoyl-1-methylpiperidine (28.16 g, 0.18 mole, 69% yield), crystallized from ethanol as a white solid (mp. 180° C.).
$^1$H-NMR (CD$_3$OD) δ 1.51 (m,2H), 2.15 (m,2H), 2.25 (s,3H), 2.4 (m,2H), 2.7 (m,2H) ppm.
Mass Spectrum m/e 158 ($M^+$).

c) 1-methylpiperidine-4-spiro-5'-(oxazolidine-2',4'-dione) AF169

To a solution of potassium methoxide (9.8 g, 0.14 mole) in dry ethanol (60 ml), was added a solution of 4-hydroxy-4-carboxamide-N-methyl piperidine (27.5 g, 0.17 mole) and diethyl carbonate (26.23 g, 0.22 mole) in ethanol (300 ml). The resulting mixture was refluxed at 80° C. for 60 hours. The reaction mixture was evaporated, the residue was shaken with cold water (70 ml) and neutralized with HCl (2N) to pH 7. The solution was concentrated to half volume and the white precipitate filtered. Trituration with ethanol yielded 1-methylpiperidine-4-spiro-5'-(oxazolidine-2',4'-dione) AF169 (22 g, 0.12 mole) in 70% yield as a white solid (mp. 285° C. (dec)).
$^1$H-NMR (D$_2$O, pH 7) 2.07 (m,2H), 2.27 (m,2H), 2.95 (s,3H), 3.30 (m,2H), 3.60 (m,2H) ppm.
Mass Spectrum (the pH of the compound is 7) m/e 185 and 184 ($M^+$+1 and $M^+$).

d) 1-methylpiperidine-4-spiro-5'-(3'-ethyloxazolidine-2',4'-dione) AF180

To a solution of 1-methylpiperidine-4-spiro-5'-(oxazolidine- 2',4'-dione) (2.8 g, 0.015 mole) in dry DMF (100 cc), potassium hydride (65% in oil) was slowly added until the reaction stopped warming up (4.9 g were used). The white suspension was refluxed for one hour and cooled. Ethyl bromide (4.6 g, 0.042 mole) was added dropwise. The reaction warmed up spontaneously. After the mixture has cooled down to room temperature, it was refluxed for two hours. After cooling, a white solid was separated and washed with ethanol. After evaporation of the solvents, the crude product was chromatographed on a silicagel column, using chloroform and methanol as eluent. The fractions containing the product were evaporated. The product was isolated and identified in the free-base form. For practical handling, it was converted to the hydrochloric acid salt with an HCl/ether/ethanol solution from which it precipitated as 1-methylpiperidine-4-spiro-5'-(3'-ethyloxazolidine-2',4'-dione), hydrogen chloride salt (0.746 g, 0.003 mole, 21% yield) (mp. 305° C. (dec)).
$^1$H-NMR (CDCl$_3$, free base) δ 1.2 (t,3H), 1.75 (m,2H), 2.15 (m,2H), 2.3 (s,3H), 2.32 (m,2H), 2.80 (m,2H), 3.55 (q,2H) ppm.
$^{13}$C-NMR (CDCl$_3$, free base) δ 13 ($\underline{C}$H$_3$CH$_2$), 32 ($\underline{C}$H$_2$CH$_3$), 35 (CH$_2$—$\underline{C}$H$_2$—C, 46 (N—$\underline{C}$H$_3$), 50 ($\underline{C}$H$_2$—N—CH$_3$), 85 ($\underline{C}$ spiro), 155 (O$\underline{C}$=O), 175 (C—$\underline{C}$=O) ppm.
Mass spectrum (free base) m/e 212 ($M^+$).

EXAMPLE 21

1-Methylpiperidine-4-spiro-4'-(2'-methyl-2'-thiazoline)

AF151(S)

a) A mixture of 1-methylpiperidine-4-spiro-4'-(2'-methyl-2'-oxazoline), AF151 (1.85 g, 11.01 mmole); phosphorus pentasulfide (1.83 g., 8.23 mmole) and p-toluenesulfonic acid monohydrate (4.20 g., 22.08 mmole) in xylene (70 ml.), was magnetically stirred and refluxed for 3 hr. The solvent was azeotropically distilled and the residue left was made basic with concentrate aqueous solution of NaOH, then extracted with dichloromethane. The organic extract was dried ($Na_2SO_4$) and the solvent was removed to give a brown oil (2.10 g.) which was chromatographed on a silica gel column (Kieselgel S, 0.032–0.063 mm., Riedel DeHaen, 70 g.). Elution with a solvent mixture of chloroform (97%)-methanol (3%) which contained 10M ammonia, gave fractions which contained pure AF151(S) (0.90 g.).

b) An intimate mixture of powders of 4-acetamido-4-hydroxymethyl-1-methylpiperidine (8.00 g., 0.043 mole) and phosphorus pentasulfide (6.10 g., 0.0275 mole) was suspended in xylene (120 ml.), magnetically stirred and refluxed fop 6 hr. The reaction mixture was left at room temperature overnight and the precipitate obtained was filtered and washed with petroleum ether (40°–60° C.) to give gray powder (13.0 g.). The powder obtained was cooled and made basic with an aqueous concentrated solution of NaOH, then extracted with dichloromethane several times. The combined extracts were dried ($Na_2SO_4$) and evaporated. The residue left was extracted with hexane and the hexane removed to give a red oil (3.53 g.) which was distilled to give colorless oil b.p. 60°–68° C. (0.4 mm.), (2.40 g.), which was chromatographed on a column of silica gel 60 (Merck, 100 g.). Elution with a solvent mixture of $CHCl_3$:$Et_2O$:MeOH:$NH_4OH$ (70:25:4:1) gave pure AF151(S) (1.71 g.).

$^1$H-NMR ($CDCl_3$) 1.65–1.78(m,2H); 1.90–2.04(m,2H); 2.19(s,$CH_3C=N-$); 2.32(s,$CH_3N-$); 2.30–2.43(m,2H); 2.60–2.75(m,2H); 3.11(s,$CH_2S-$) ppm.
$^{13}$C-NMR ($CDCl_3$) 19.9($\underline{CH}_3C=N-$); 35.8($C_3$&$C_5$); 43.1($-CH_2S-$); 45.6($CH_3N-$); 52.1($C_2$&$C_6$); 78.5($C_4$); 161.0($S-C=N-$) ppm. MS m/e 184($M^+$, 100%); 110(26%); 109(56%); 72(93%); 71(24%).

EXAMPLE 22

1-Methylpiperidine-4-spiro-4'(5)'-(2'-methyl-2'-imidazoline)

AF190 a) 4-amino-4-cyano-1-methylpiperidine

1-Methylpiperidin-4-one (33.0 g, 0.292 mole), potassium cyanide (19.5 g, 0.299 mole) and ammonium chloride (16.5 g, 0.308 mole) were suspended in methanol (225 ml) and water (150 ml) and the mixture was stirred at room temperature for 12 days. The precipitate obtained was filtered and the filtrate was evaporated under reduced pressure. To remove water which may have remained in the residue, ethanol was added to it and then azeotropically distilled. Ethanol was added again to the residue, which dissolved in part and left an inorganic solid which was filtered and washed with ethanol. The filtrate and washings were combined and the solvent removed to leave a viscous oil (35.5 g) which showed two spots on TLC (chloroform:methanol:ammonium hydroxide (aq.) 17:2:1 - silica gel). It was crystallized from ether to give a solid which was further crystallized from the same solvent to give 4-cyano-4-hydroxy-1-methylpiperidine as crystals m.p. 130°–133° C. The mother liquor when concentrated deposited a second crop of a crystalline solid which was mostly 4-amino-4-cyano-1-methylpiperidine.

$^1$H-NMR ($CDCl_3$) 1.72–1.88 (m,2H); 2.01 (m,2H); 2.25–2.37(m,2H); 2.32(s,$CH_3N-$); 2.74–2.83(m,2H) ppm. MS m/e 139($M^+$); 112($M^+$-HCN); 71; 70.

The 4-amino-4-cyano-1-methylpiperidine upon acetylation with acetic anhydride and pyridine gave 4-acetamido-4-cyano-1-methylpiperidine which was crystallized from petroleum ether-dichloromethan m.p. 143°–144 C.
$^1$H-NMR ($CDCl_3$) 1.78–1.96 (m,2H); 2.04 (s,$CH_3CON-$); 2.32 (s,$CH_3N-$); 2.35–2.50 (m,4H); 2.66–2.84 (m,2H); 6.22 (s, $-NHCO-$) ppm.
MS m/e 181 ($M^+$); 122 ($M^+-CH_3CONH_2$)
IR($CHCl_3$) 3438, 3303, 2940, 2804; 2242 ($C\equiv N$); 1670 (amide) $cm^{-1}$. Acid hydrolysis ($H_2SO_4$) of the 4-amino-4-cyano-1-methylpiperidine gave 4-amino-4-carbamoyl-1-methylpiperidine which was crystallized from ethylacetate-dichloromethane m.p. 145°–147° C.
$^1$H-NMR ($CDCl_3$) 1.44 (m,2H); 1.68 (br—$NH_2$); 2.12–2.34 (m,4H); 2.30 (s, $CH_3N-$); 2.70–2.82 (m,2H); 5.47 (br —NH—); 7.39 (br, —NH—) ppm.
MS m/e 158 ($M^+$+1); 157 ($M^+$); 140 ($M^+-NH_3$, 100%); 113 ($M^+$- $CONH_2$), 96; 71.

b) 4-amino-4-aminomethyl-1-methylpiperidine

A solution of 4-amino-4-cyano-1-methylpiperidine (3.60 g) in dry dimethoxyethane was added to mechanically stirred suspension of $LiAlH_4$ (3.0 g) in dry dimethoxyethane under nitrogen atmosphere, at such a rate that the temperature didn't rise over 50° C. At the end of the addition the mixture was heated under reflux for 6 hr. Excess $LiAlH_4$ was destroyed by adding to the cold (0° C.) stirred reaction mixture, under nitrogen, 4M NaOH (10 ml), water (3 ml), saturated NaOH solution (10 ml) and water (5 ml). The organic solvent was separated and the aqueous phase was extracted several times with hot THF. The organic solvent which was separated and the THF extracts were combined, dried ($Na_2SO_4$) and the solvents were removed to give the title compound as a viscous oil (3.17 g) which was purified by distillation b.p. 60°–62° C. (0.8 mm).
$^1$H-NMR ($CDCl_3$) 1,43 (m, 2H); 1.58 (m, 2H); 2.15 (br.—$NH_2$) 2.30 (s, $CH_3N-$); 2.30 (m, 2H); 2.56 (s, —$\underline{CH}_2NH_2$); 2.56 (m, 2H) ppm. Acetylation of the diamine obtained gave diacetamide as a solid m.p. 175°–176° C. (from acetonitrile).
$^1$H-NMR ($CDCl_3$) 1.74 (m, 2H); 1.96–2.10 (m, 2H); 1.99 (s, $CH_3CON-$); 2.02 ($CH_3CON-$); 2.21 (m, 2H); 2.28 (s, $CH_3N-$); 2.51–2.61 (m, 2H); 3.50 (d, J=5.7 Hz, —$CH_2NH-$); 5.62 (s, —NHCO—); 7.18 (t, —$CH_2$ NHCO—) ppm.
MS m/e 227 ($M^+$); 184 ($M^+-CH_3CO$); 169 ($M^+-CH_3CONH$); 168 ($M^+-CH_3CONH_2$); 167; 155; 112; 109 (100%); 96; 71; 70.

The diacetamide was also obtained by hydrogenation of 4-amino-4-cyano-1-methylpiperidine with hydrogen (50 psi) with Raney-Ni as catalyst in hot (60° C.) acetic anhydride containing sodium acetate.

c) 1-Methylpiperidine-4-spiro-4'(5)'-(2'-methyl-2'-imidazoline) AF190.

To a solution of b) 4-amino-4-aminomethyl-1-methylpiperidine (0.248 g., 1,734 mmole) in dichloromethane (5 ml), ethyl acetimidate hydrochloride (0,282 g., 2.282 mmole) was added and the mixture was stirred at room temperature for 3 hr. The solvent was removed under reduced pressure and the residue was made basic with concentrate aqueous $Na_2CO_3$ solution, then extracted with dichloromethane. The extract was dried (Na$_2$CO$_3$) and the solvent was removed to give a colorless oil (191 mg), which was chromatographed on a column of silica gel. Elution with a solvent mixture of methanol: chloroform: 1% ammonium hydroxide (aq.), while increasing the methanol content from 10% to 99% gave pure product AF190 as an oil which solidified upon refrigeration.

$^1$H-NMR (CDCl$_3$) 1.57–1.84 (m, 4H); 1.93 (s, CH$_3$C=N—) 2.17–2.33 (m, 2H); 2.29 (s, CH$_3$N—); 2.56 (m, 2H); 3.37 (s, —CH$_2$—N—) ppm.
$^{13}$C-NMR (CDCl$_3$) 15.2 (CH$_3$C=N—); 37.3 (C$_3$ & C$_5$); 46.1 (CH$_3$N—); 52.5 (C$_2$ & C$_6$); 59.7 (C$_4$); 63.7 (—CH$_2$N—); 162.1 (—C=N—) ppm.
MS m/e 167 (M$^+$); 152 (M—CH$_3$); 138; 109 (100%); 97; 96; 72; 71; 70.
IR (neat) 3260; 2933; 2852; 2800; 1620 (—C=N—) cm$^{-1}$.

EXAMPLE 23

1-methylpiperidine-4-spiro-4'(5')-[2'-methyl-4'H(5'H)-imidazol-5'(4')-one]AF230

4-acetamido-4-cyano-1-methylpiperidine (1.03 g) was dissolved in concentrated sulfuric acid (4.0 ml) and left at room temperature for 4 days. The reaction mixture was added to cold water (10 ml) and then barium carbonate was added until no reaction was evident. The precipitated barium sulfate was filtered off, and washed with water and ethanol. The pH of the combined filtrate and washings was adjusted to 13 with concentrated NaOH solution, and the solvents were removed under reduced pressure. The residue was extracted with ethanol, the extract was evaporated, the residue was extracted with dichloromethane, and the extract was evaporated to give an oil (0.75 g), which was chromatographed on a column of silicagel 60 (Merck 0.040–0.063 mm, 32 g). Elution with 1:9 methanol (containing 15% w/w NH$_3$)-chloroform gave pure AF230 (0.185 g), crystallized from dichloromethane-ether m.p. 231°–234° C.
$^1$H-NMR (CDCl$_3$) δ 1.49(m,2H), 1.97(m,2H), 2.20(s,CH$_3$—), 2.34(s,CH$_3$ 2.48(m,2H), 2.80(m,2H), 9.83(br.—NH—) ppm.
$^1$H-NMR (D$_2$O) δ1.55(m,2H), 1.88(m,2H), 2.22(s,CH$_3$—), 2.29(s,CH$_3$—), 2.33(m,2H), 2.90(m,2H) ppm.
MS m/e 181 (M$^+$); 111 (M$^+$–70); 104; 94; 77; 71(100%); 70.
UV (EtOH) lambda$_{max}$. 224 nm. ($\epsilon$4650), 248 nm. ($\epsilon$2450).
IR (KBr) 3140; 2795; 2540; 1665; 1540 cm$^{-1}$.

Cyclization of 4-acetamido-4-cyano-1-methylpiperidine could also be effected in basic media. Thus, reflux of this compound in 1N ethanolic KOH or in aqueous 1N NaOH also gave AF230. In the latter case, there was also obtained 4-acetamido-4-carbamoyl-1-methylpiperidine, m.p. 207°––208° C. (dec.), crystallized from dichloromethane-methanol.
$^1$H-NMR (CDCl$_3$) δ 2.05(CH$_3$CO—), 2.08–2.30 (m,6H), 2.28 (CH$_3$N—), 2.63(m,CH$_2$—), 5.40(brs, —NH—), 5.56 (brs, —NH—), 7.04 (brs, —NH—) ppm.
MS m/e 199 (M$^+$); 181 (M$^+$–H$_2$O); 155 (M$^+$-CONH$_2$); 140 (M$^+$-CH$_2$CONH$_2$); 122, 112, 111; 96; 71(100%); 70.

AF230 may exist in the form of tautomers, as indicated by the title.

EXAMPLE 24

1-methylpiperidine-4-spiro-5'-(2'-methyl-2'-oxazoline-4'-one),

AF238
(a) 4-acetamidocarbonyl-4-acetoxy-1-methylpiperidine

To a mixture of 4-cyano-4-hydroxy-1-methylpiperidine (2.55 g, 18 mmole) and acetic anhydride (11 ml, 108 mmoles) in a three-necked flask, 5.1 g (2 equivalents) of a 60% solution of perchloric acid (HClO$_4$) was added dropwise. An exothermic reaction occurred, but the temperature dropped after 20 minutes. The solution was stirred for 2 hours, and was left standing overnight at room temperature. The white precipitate was filtered off and washed with ether and petroleum ether. The perchloric acid salt of 4-acetamidocarbonyl-4-acetoxy-1-methylpiperidine was obtained in almost quantitative yield.
$^1$H-NMR [perchlorate] (D$_2$O) δ2.2-2.4(m,2H), 2.26(s,3H), 2.27(s,3H), 2.5(m,2H), 2.95(s,3H), 3.32(m,2H), 3.58(m,H) ppm.
$^1$H-NMR [free base] (CDCl$_3$) δ2.05-2.27(m,4H), 2.13(s, 3H), 2.28(s,3H), 2.67–2.75(m,4H), 8.4(bs,1H,NH) ppm.
MS m/e 242 (M$^+$); 182, 167, 139, 123(100%), 114, 96, 82, 70, 60.
UV (H$_2$O) lambda$_{max}$. 206 nm. ($\epsilon$20400).
IR (KBr) 3380, 3020, 1740, 1670(sh), 1550, 1400, 1380, 1250 cm$^{-1}$.
(b) 1-methylpiperidine-4-spiro-5'-(2'-methyl-2'-oxazoline-4'-one), AF238.

The perchloric acid salt of 4-acetamidocarbonyl-4-acetoxy-1-methylpiperidine (70 mg, 0.25 mmole) in xylene was heated at 172° C. (silicone oil bath temperature), whereupon the white suspended solid turned yellow. A strong smell of acetic acid was perceptible in the course of the reaction. TLC shows total conversion to 1-methylpiperidine-4-spiro-5'-(2'-methyl-2'-oxazoline-4'-one), AF238, which was characterized as the perchloric acid salt.
$^1$H-NMR (D$_2$O) δ2.2(m,3H), 2.25(m,2H), 2.45(m,2H), 2.8(s,3H), 3.25(m,2H), 3.5(m,2H) ppm.
MS m/e 182 (M$^+$); 140, 123, 112, 104, 96, 77, 70(100%).

EXAMPLE 25

1-methylpiperidine-4-spiro-5'-(1'-methyl-3'-ethylhydantoin),

AF161

To a mixture of AF160 (100 mg, 0.47 mmole) and KH (100 mg, 35% w/w in mineral oil) in 5 ml DMF, was added methyl p-toluenesulfonate (0.4 g, 1 mmole), the solution was stirred 10 minutes at room temperature, and acidified with oxalic acid in ether. The precipitate was dissolved in water, basified, and extracted with petroleum ether, and the extracts were concentrated and chromatographed on silica using 90:10:1 chloroform/methanol/aqueous ammonia. The pure fractions were combined and evaporated, and the residue was dissolved in ether and precipitated as an HCl salt (85 mg, yield 72%).
$^1$H-NMR (free base, CDCl$_3$) δ1.2(t,J=6 Hz,3H), 1.6-1.65(m, 2H), 2.0-2.1(m,2H), 2.39(s,3H), 2.75–2.85(m,4H), 2.86(s, 3H), 3.55(q,J=6 Hz,2H) ppm. $^1$H-NMR (HCl salt, D$_2$O) δ1.2(t,J=6 Hz,3H), 2.1-2.15(m,2H), 2.3-2.4(m,2H), 2.95(s, 3H), 3.0(s,3H), 3.5(q,J=6 Hz,2H) ppm.
MS m/e 225 (M$^+$18%); 71(100%).

EXAMPLE 26

1—methylpiperidine-4-spiro-5'-(1',3'-diethylhydantoin),

AF162

To a mixture of 1—methylpiperidine-4-spiro-5'-hydantoin (110 mg, 0.6 mmole) and KH (0.2 g, 35% in mineral oil w/w) in 3 ml DMF, there was added ethyl bromide (0.5 g, 4.6 mmole), the solution was stirred 30 minutes at room temperature, diluted with ether and acidified with excess oxalic acid. The precipitate was dissolved in water, basified, and extracted several times with chloroform, and the extracts were combined, concentrated and chromatographed on silica gel using a gradient of chloroform and 90:10:1 chloroform/methanol/aqueous ammonia, to give pure AF162 (60 mg, yield 42%).

$^1$H—NMR (free base, CDCl$_3$) δ 1.2(t,J=6 Hz,6H), 1.65–1.7(m,2H), 1.96–2.15(m,2H), 2.4(s,3H), 2.5–2.6(m, 4H), 3.3(q,J=6 Hz,2H) ppm.

$^1$H—NMR (HCl salt, D$_2$O) δ 1.15(t,J=6 Hz,6H), 2.05–2.15(m,2H), 2.25–2.35(m,2H), 2.9(s,3H), 3.3(q,J=6 Hz,3H) ppm.

$^{13}$C—NMR (HCl salt, D$_2$)O δ 14.0; 28.6; 35.0; 44.0; 52.7; 59.2; 157.0; 177.0 ppm. MS m/e 239 (M$^+$75%); 71 (100%).

EXAMPLE 27

1—Methylpiperidine-4-spiro-4'-(2'-methylthio-5'-methoxy-4'H-imidazole) AF191

1—Methylpiperidine-4-spiro-4'-(2', 5'-dimethylthio-4'H-imidazole) AF177 (0.700g, 2.881 mmole) and sodium methoxide (0.360g, 6.667 mmole) were heated under reflux in methanol (15 ml) for 3.5 hours. Evolution of gas was observed. The solvent was removed from the reaction mixture and the residue was extracted with dichloromethane. The organic extract was evaporated to give a solid residue (0.613g), which was extracted with hot petroleum ether. The solvent was evaporated from the extract to leave a residue (0.263g), which on crystallization from petroleum ether gave pure AF191, m.p. 84°–85° C.

$^1$H—NMR(CDCl$_3$) 1.40(m,2H); 1.97 (m,2H); 2.36(s, CH$_3$N—); 2.52(s,CH3S—); 2.53(m,2H); 2.70–2.80(m,2H); 4.10(s,CH$_3$O—) ppm.

$^{13}$C-NMR(CDCl$_3$) 13.6(CH$_3$S—); 32.3(C$_3$); 46.2(CH$_3$N—); 51.9(C$_2$); 57.9(CH$_3$O—); 74.2(C4); 171.6(—N=$\underline{C}$-SCH$_3$); 196.0(—N=$\underline{C}$-OCH$_3$) ppm.
MS m/e 228 M$^+$+1).

EXAMPLE 28

1—Methylpiperidine-4-spiro-4'-(2'-methylthio-5'-amino-4'H-imidazole) AF192

A solution of AF177 (0.411g) in a reagent (15 ml) prepared by dissolving ammonia in methanol (15% w/w) was stirred 3 days at room temperature. The reaction mixture was evaporated and a fresh 15 ml portion of the reagent was added to the residue, and the reaction was repeated 2×more. Finally, the reaction mixture was evaporated under reduced pressure, and the solid residue was washed with acetone to give AF192, a white solid (0.266g). After crystallization from ethanol, the m.p. was >240° C. (dec.).

$^1$H-NMR(D$_2$O) 1.48(m,2H); 1.89 (m,2H); 2.29(s,CH$_3$N-); 2.46(m,2H); 2.48(s,CH$_3$S—); 2.86(m,2H) ppm.
MS m/e 212 M+); 142 (M+- 70); 70.

EXAMPLE 29

1—Methylpiperidine-4-spiro-4'-(2'-methylthio-5'-aminomethyl- 4'H-imidazol)AF193 and 1—methylpiperidine-4-spiro-4'-(2 ', 5'-bis(aminomethyl)-4'H-imidazole)

AF194

A solution of AF177 (0.338g) in aqueous methylamine (5.0ml; 35%) was heated at 80° C. for 2 hours. The water and excess reagent were removed by evaporation under reduced pressure and the residue was chromatographed on a column of silicagel (Merck 60, 0.040-0.06mm). Elution with an 80:20:1 solvent mixture of chloroform/methanol/aq. ammonia gave AF193 as a white solid (0.061 g). Crystallization from acetonitrile gave m.p. 193°–194° C.

$^1$H-NMR(CDCl$_3$) 1.44(m,2H); 1.85 (m,2H); 2.38(s,CH$_3$N-); 2.52(s,CH$_3$S-); 2.66(m,2H); 2.81(m,2H); 3.06(s,CH$_3$NH—); 6.47(—NH—) ppm.
MS m/e 226 M+); 179(M+—CH$_3$S); 170 (M+—CH$_3$NHCN); 169; 156(M+-70).

Elution with an 50:50:1 solvent mixture of chloroform/methanol/aq. ammonia gave AF194 as a white solid (0.130 Crystallization from acetonitrile gave m.p. 113°–114° C.
$^1$H-NMR(CDCl$_3$+CD$_3$OD) 1.44(m,2H); 1.81 (m,2H); 2.37(s,CH$_3$N—); 2.57(m, 2.80(m,2H); 2.95(s,CH$_3$NH—); 2.96(m,CH$_3$NH—) ppm.
MS m/e 209 M+); 152; 139(M+—70).

When repeating the above reaction, but using two moles of methylamine for each mole of AF177, the main product obtained was AF193, with only traces of AF194.

EXAMPLE 30

1—Methylpiperidine-4-spiro-4'-(2'-methyl-2'-oxazoline) AF150

(a) 1-Methyl-4-nitromethylpiperidin-4-ol hydrochloride

This starting material was prepared using a slight modification of the method of A.D. Cale (U.S. Pat. No. 4,746,655, 1988). A mixture of N-methylpiperidinone (142 g., 1.28 mole) and nitromethane (78.1 g., 1.28 mole), was added to a well-stirred solution of sodium ethoxide (1.28 mole), 20% in ethanol, maintaining the internal temperature at 5°–8° C. A white solid precipitates, the stirring is continued for 20 minutes and another 40 minutes at room temperature. The resulting solution was acidified with 500 ml. of 7.2N HCl in isopropyl alcohol. The hydrochloride and the inorganic salts were extracted with CH$_3$OH (3×200 ml) and the solvent removed in vacuo to give the title compound, m.p. 180°–182° C. (non hygroscopic).
m/z: 174 (M$^+$of free base, 100%), 157 (M—OH, 20%), 127 (M-H-NO$_2$, 25%), 113 (M-NO$_2$-CH$_3$, 40%).

(b) 4—Aminomethyl-l-methylpiperidin-4-ol hydrochloride

Palladium on charcoal (10%, 4 g.) was added portionwise to a solution of 1—methyl-4-nitromethylpiperidin-4-ol (133.5 g.) in methanol (1500 ml). The compound was hydrogenated in a Paar at a pressure of 55 psi at room temperature for 48 hours. The solution was cautiously filtered, treated with active charcoal, the solvent removed and the residue was triturated with ethanol (200 ml.) to give the title compound, m.p. 177°–179° C.
m/z: 144(M$^+$of free base, 15%), 127 (M—OH, 25%), 114 (M—CH$_2$NH$_2$, 100%).

(c) 1—Methylpiperidine-4-spiro-4'-(2'-methyl-2'-oxazoline) AF150

A solution of KOH (1.43 g. of 86%) in methanol (50 ml.) was added to a solution of 4-aminomethyl-l-methylpiperidin-4-ol hydrochloride (3.61 g., 0.02 mole) in absolute methanol (50 ml.). After stirring for 10 minutes, a solution of ethyl acetimidate hydrochloride (2.7 g.) in 20 ml. absolute methanol was added, and stirring continued for 30 minutes at room temperature. The solvent was removed, and the residual solid was dissolved in a solution of 2.8 g. Na$_2$CO$_3$ in 50 ml. water, which was concentrated to dryness in vacuo.

The white solid was extracted with 2 ×50 ml. chloroform, treated with active charcoal, dried (Na$_2$SO$_4$) and the solvent removed to afford the title product (62.5% yield), m.p. 45° C. (sublimed at 40° C./0.05 mm Hg), giving a single spot on silica TLC eluted with 2% NH$_3$ in CH$_3$OH, Rf=0.4.
m/z: 168 (M$^+$of free base, 100% at 7.5 ev).
$^1$H—NMR (300 MHz, CDCl$_3$): δ 3.56 (2H, q, J=1.5 Hz), 2.53 (4H, m), 2.34 (3H,s), 1.96 (3H, t, J=1.5 Hz), 1.82 (4H, m).

Replacement of the KOH used in this Example by the equivalent amount of NaOH or Et$_3$N, gave similar results.

(d) AF150—dibenzoyl-D-tartrate

A hot solution of dibenzoyl-D-tartaric acid (5.4 g., 15 mmole) in 500 ml. toluene was added while stirring to AF150 (5.5 g., 32 mmole) dissolved in 200 ml. dry toluene. The precipitate was allowed to settle and the supernatant liquid was decanted off. The residual solid was washed with 3 ×100 mi. dry toluene and dried under reduced pressure to afford 8.4 g. (80% yield) of a white slightly hygroscopic solid. TLC chloroform/alumina (Merck Art 5581) Rf=0.4.
m/z: 168 (M$^+$)
$^1$H—NMR (300 MHz, D$_2$O containing 1.5 mg. Na$_2$CO$_{3/0.5}$ ml. D$_2$O): δ1.95 (s, 6H, CH$_3$—C), 2.35 (s, 6H, CH$_3$—N), 3.5 (s, 4H, CH$_2$), 5.7 (s, 2H), 7.5-8.2 (m, 10H, aromatic hydrogens).

EXAMPLE 31

1—Methylpiperidine-4-spiro-4'-(2'-ethyl-2'-oxazoline)
(2'-ethyl analog of AF150)

This compound was prepared similarly to the compound of Example 31, using the equivalent amount of ethyl propionimidate hydrochloride, in place of ethyl acetimidate hydrochloride. The product was obtained as a liquid, b.p. 53°/0.03 mm Hg, in 60.5% yield.
$^1$H—NMR (300 MHz, CDCl$_3$): δ3.52 (2H, t, J=1.5 Hz), 2.47 (4H, m), 2.30 (3H, s), 2.26 [2H, quartet (J=7 Hz), triplets (J=1.5 Hz)], 1.86 (2H, m), 1.72 (2H, m), 1.18 (3H, t).

EXAMPLE 32

1-Methylpiperidine-4-spiro-5'-(2'-methyl-2'-oxazoline)
AF151

(a) 1-Methylpiperidine-4-spiro-5'-hydantoin

A mixture of solutions of 1-methylpiperidine-4-one (36.44 g., 0.322 mole) in ethanol (150 ml.), ammonium carbonate (93.0 g., 0.968 mole) in water (400 ml.) and potassium cyanide (25.8 g., 0.396 mole) in water (82 ml.), was heated at 60° C. for 2.5 hours and then left at room temperature overnight, when 1-methylpiperidine-4-spiro-5'-hydantoin separated. It was filtered off and washed with small amounts of cold water, ethanol and ether, to give a crystalline powder (27.0 g.). Concentration of the filtrate and washings gave a second crop (20.0 g.). The product was crystallized from methanol: m.p. 265°–276° (dec.).
IR (KBr) 3170 (NH); 1700 (C=O) cm$^{-1}$ m/z 183(M$^+$, 38%); 71 (100%)
$^1$H—NMR (300 MHz, D$_2$O): δ 1.8 (2H), 2.06 (sextet, 2H), 2.49 (S, —CH 3), 2.58 (t, 2H), 3.14 (t, 1H), 3.20 (t, 1H). (b) 4-Amino-1-methylpiperidine-4-carboxylic acid 1-methylpiperidine-4-spiro-5'-hydantoin (9.75 g., 0.0533 mole) and barium hydroxide octahydrate (28.8 g., 0.00913 mole) in water (150 ml.) were heated at 160° C. in an autoclave for three hours. The contents of four such batches were combined and the precipitated barium carbonate was filtered off. The liltrate was neutralized with solid carbon dioxide and the precipitate was removed by filtration. The liltrate was concentrated to a small volume to give 4-amino-l-methylpiperidine-4-carboxylic acid (32.0 g., 95% yield), m.p. 275°–280° C. (dec.).
IR (KBr) 3300, 1655, 1580 cm$^{-1}$ m/z 158(M$^+$, 90%); 141 (98%, M—OH); 113 (12%, M—CO$_2$H); 96 (100%); 71 (52%)
$^1$H—NMR (300 MHz, C$_5$D$_5$N +D$_2$O): δ 1.2 (m, 2H), 1.48 (s, CH$_3$N-), 1.7 1.9 (m, 2H), 2.0 (m, 2H).

(c) 4-Amino-4-hydroxymethyl-1-methylpiperidine

Lithium aluminum hydride powder (15.62 g., 0.412 mole) in dry tetrahydrofuran (THF) (600 ml.) was heated under reflux for 15 minutes, after which 4-amino-1-methylpiperidine-4-carboxylic acid (31.0 g., 0.196 mole) in the form of a dry powder was added portionwise under nitrogen, with efficient stirring. After the addition was completed, the reaction mixture was heated under reflux for four hours, cooled to 0° C. under nitrogen with efficient stirring, worked up by careful slow addition of water (20 ml.), 15% aqueous NaOH (20 ml.) and again water (10 ml.). The reaction mixture was filtered and the precipitate was extracted with boiling THF (3 ×150 ml.). The THF liltrate and the extracts were combined and the solvent removed at 25 mm to give a yellow viscous oil (28.0 g., 98.9% yield).
IR (neat) 3320 (NH), 3200 (br. OH), 1587 (NH$_2$), 1468, 1448 cm$^-$
m/z 144(M$^+$, 15%); 127 (M—OH); 113 (M—C$_2$OH); 96 (100%); 70 (41%).
$^1$H—NMR (300 MHz, CDCl$_3$): δ 1.41 (m, 2H), 1.60 (m, 2H), 2.24 (s, CH$_3$—N), 2.29 (m, 2H), 2.48 (m, 2H), 2.50 (br., —NH$_2$), 3.29 (s, —CH$_2$OH).

(d) 1-Methylpiperidine-4-spiro-5'-(2'-methyl-2'-oxazoline) AF151

A mixture of 4-amino-4-hydroxymethyl-1-methylpiperidine (1.80 g.) with acetic acid (20 mi.) and xylene (20 mi.) was azeotropically distilled for 28 hours. The remaining acetic acid and xylene were removed at reduced pressure (25 mm Hg) to leave a residual viscous oil which was basified to pH 11 with an aqueous solution of K$_2$CO$_3$. Extraction with chloroform and evaporation of the extract gave a small amount of residual brown oil (0.27 g.). The aqueous solution remaining after chloroform extraction was evaporated to remove water, the residual solid was extracted with chloroform and the extract was dried (Na$_2$SO$_4$) and evaporated, to afford as residue a very hygroscopic solid (3.0 g.). TLC showed that the latter gave mainly one spot, which was more polar than the starting amino-alcohol. A portion of the hygroscopic solid, which melted at 150°–160° C., was heated under vacuum, and almost immediately began to distil as a colorless oil at 45° C./0.15 mm Hg. This oil, on keeping in the freezer, formed crystalline needles melting at room temperature. The distillate was the acetic acid salt of the title compound.
IR (neat) 1664 (—C=N); 1565 & 1398 (—CO$_2$—); 1256 (C—O) cm$^{-1}$
m/z 168(M$^+$of free base); 109; 70.
$^1$H—NMR (300 MHz, CDCl$_3$): δ 1.77 (m, 2H), 1.96 (m, 2H), 1.98 (s, CH$_3$—), 2.0 (s, CH$_3$—), 2.49 (s, CH$_3$—N—), 2.91 (m, 4H), 3.95 (s, —CH $_{20}$O—), 9.30 (br. s,
$^{13}$C-NMR (300 MHz, CDCl$_3$): δ 14.0 (CH$_3$CO$_2$-), 22.9 (CH$_3$C=N-), 35.6 (C$_3$ and C$_5$), 44.4 (CH$_3$N+), 51.1 (C$_2$ and C$_6$), 67.0 (C$_4$), 77.4 (C$_5$·), 164.3 (C—=N), 176.7 (—CO$_2$—).
$^1$H—NMR of free base (300 MHz, CDCl$_3$): δ 1.64 (m, 2H), 1.84 (m, 2H), 1.98 (s, CH$_3$—), 2.26 (m, 2H), 2.30 (s, CH$_3$—), 2.69 (m, 2H), 3.94 (s, —CH$_2$—).

EXAMPLE 33

1—Methylpiperidine-4-spiro-5'-(2'-ethyl-2'-oxazoline)

(2'-ethyl analog of AF151)

A mixture of 4-amino-4-hydroxymethyl-1-methylpiperidine (3.0 g.) with propionic acid (50 ml.) and xylene (90 ml.) was azeotropically distilled for 5 hours. The residue (7 mi.) was basified to pH 11–12 with an aqueous solution of $K_2CO_3$. Extraction with chloroform and evaporation of the extract gave a mixture of non-polar compounds (0.80 g.). The aqueous solution remaining after chloroform extraction was evaporated to remove water, the residual solid was extracted with chloroform and the extract was dried ($Na_2SO_4$) and evaporated, to afford as residue a hygroscopic solid (3.6 g.). TLC showed that the latter gave mainly one spot, which was more polar than the starting amino-alcohol (silica gel, solvent 40:58:2 methanol-chloroform-aqueous ammonia). A portion of the hygroscopic solid (1.5 g.) was heated under vacuum, and almost immediately began to distil as a viscous colorless oil at 50° C./0.1 mm Hg. The distillate is the propionic acid salt of the title compound.

m/z 182($M^+$of free base, 14%); 167 (5%), 154 (71%), 125 (9%), 109 (10096 (45%), 81 (30%), 74 (57%), 70 (89%), 57 (64%).

$^1$H-NMR ( 300 MHz, $CDCl_3$ ): δ 1.12 ( t, J=7.5 Hz, C$\underline{H}$CH$_2$—), 1.17 ( t, J=7.6 Hz, C$\underline{H_3}$CH$_2$—), 1.75 (m, 2H), 2.00 (m, 2H), 2.29 (q, J=7.5, CH$_3$C$\underline{H_2}$—), 2.30 (q, J=7.6, CH$_3$C$\underline{H_2}$—), 2.56 (s, CH$_3$N—), 3.02 (m, 2—CH$_2$—), 3.95 (s, —CH$_2$ O—), 7.52 (br. —CO$_2$H).

To a stirred solution of the above propionic acid salt (700 mg.) in chloroform, a saturated aqueous solution of $K_2CO_3$ was added until evolution of $CO_2$ had ceased. The mixture was then stirred for 0.5 hour and the phases were separated. The aqueous phase was extracted with chloroform, the combined separated chloroform phase and the extracts were dried ($Na_2SO_4$), and the solvent was evaporated to afford the title compound in free base form as a residual colorless oil (550 mg.), which showed a single spot on TLC.

$^1$H—NMR (300 MHz, $CDCl_3$): δ 1.17 (t, J=7.6 Hz, C$\underline{H_3}$CH$_2$—), 1.61 (m, —CH$_2$—), 1.86 (m, —CH$_2$—), 2.18 (m, —CH$_2$—), 2.29 (q, J=7.6, CH$_3$C$\underline{H_2}$—), 2.30 (s, CH$_3$N—), 2.71 (m, —CH$_2$—), 3.94 (s, —CH$_2$O—).

m/z 182($M^+$25%), 167 (9%), 154 (78%), 125 (17%), 109 (100%), 96 (65%), 81 (54%), 70 (96%), 57 (77%).

An alternative route to compounds such as AF150 and AF151 depends on the cyclodehydration of the appropriate amides. Dehydrating agents such as $P_2O_5$, sulfuric acid, $BF_3$-etherate, $CaCl_2$, and molecular sieves, can be used for the above reactions. Corresponding thiazolines instead of oxazolines can be obtained by analogous reactions using $P_2S_5$.

EXAMPLE 34

1—Methylpiperidine-4-spiro-5'-(2'-methyl-2'-thiazoline) AF150(S)

(a) 4-Acetamidomethyl-4-hydroxy-1-methylpiperidine

4-Aminomethyl-4-hydroxy-1-methylpiperidine (0.83 g., 5.7 mmole) was dissolved in 10 ml. chloroform, and acetic anhydride (0.58 g., 5.7 mmole) was added. The reaction mixture warmed spontaneously to 40°-50° C. After 30 minutes, the solvent was evaporated and the crude residue was chromatographed on a silica gel column (Merck 7734), using 33:67 2% aqueous ammonia-methanol as eluent.

m/z 186 ($M^+$)

$^1$H—NMR (300 MHz, $CDCl_3$): δ 1.60 (multiplet, 4H, H3 and H4), 2.01 (singlet, 3H, CH$_3$—C), 2.29 (singlet, 3H, CH$_3$—N), 2.38 (multiplet, 2H, H1), 2.55 (multiplet, 2H, H2), 2.98 (multiplet, 1H, NH), 3.26 (doublet, 2H, H5) ppm.

$^1$H—NMR (300 MHz, $D_2O$): δ 1.42 (multiplet, 4H, H3 and H4), 1.81 (singlet, 3H, CH$_3$—C), 2.08 (singlet, 3H, CH$_3$—N), 2.27 (multiplet, 2H, H1), 2.46 (multiplet, 2H, H2), 3.03 (singlet, 2H, H) ppm. The impurity gives a peak at 3.44 ppm.

(b) 1—Methylpiperidine-4-spiro-5'-(2'-methyl-2'-thiazoline) AF150(S)

A mixture of 4-acetamidomethyl-4-hydroxy-1-methylpiperidine (6.5 g., 35 mmole) with phosphorus pentasulfide (10 g., 22 mole) was heated at 220° C. for 30 minutes, cooled, and dissolved in 30 ml. concentrated hydrochloric acid. The acidic solution was transferred to 100 ml. cold concentrated aqueous sodium hydroxide, extracted with 2 ×100 ml. chloroform, and the combined extracts were dried and evaporated to afford 5 g. of a black oily residue, which was purified by distillation at 75° C./1 mm Hg to yield 1.8 g. clear liquid.

m/z: 184 ($M^+$)

$^1$H—NMR (300 MHz, $CDCl_3$): δ 1.8–2.0 (m, 4H), 2.17 (t, 3H, CH$_3$—C), 2.2 (s, 3H, CH$_3$—N), 3.9 (q, 2H, CH$_2$-thiazoline ring). The compound according to the invention exhibit pharmacological activity and are there-fore useful as pharmaceuticals, e.g. for therapy. The spiro-compounds provided by the present invention have central and peripheral (or both) activity on the nervous system. One common characteristic activity is on the cholinergic system where the compounds are ligands (e.g. agonists or antagonists) on the muscarinic receptors. The agonistic or antagonistic profile of the compounds was evaluated in a number of tests including computer-assisted molecular evaluation, biological testing in vitro and in vivo. Computer-assisted molecular evaluation For muscarinic agonistic activity a pharmacophoric model, based on examination of numerous agonists, was constructed. The model includes definition of those parts, in the structure of the agonists that are essential for activity, their mutual spacial orientation and to some extent the maximal volume allowed for a ligand to be an agonist.

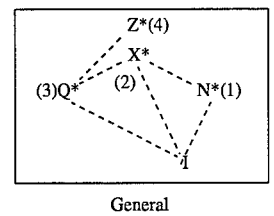

General

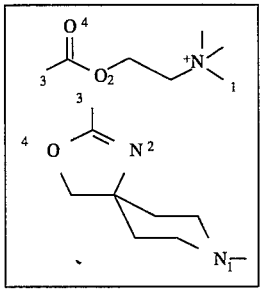

Examples

Point r is a negative charge interacting with the cationic head of the agonist. Its position relative to the nitrogen is defined in the model. Important distances (D) are as follows: D(r–$N^*$)=3.0; D(r–$X^*$)=6.50; D(r–$Q^*$)=8.70; D($x^*$–$Q^*$)= 2.45. The optimal dihedral angle r–$x^*$–$Q^*$–z =–85. Deviation from those optimal model parameters within certain limits does not abolish activity (Table #1 ).

Certain important features of this model are listed below:

1. The model allows to distinguish between full and partial muscarinic agonists. The distinction is based upon correlation between the distance r-X and agonistic efficacy.

2. The nature of the atom in position 4, corresponding to the carbonyl oxygen in acetylcholine can vary considerably as well as the dihedral angle r-x*-Q*-z* within the class of muscarinic agonists.

3. When the distance r–Q* becomes too large for agonistic activity, weakly binding antagonists are obtained.

From this model prediction regarding receptor subtype specificity of a muscarinic agonist can be made, based upon the agonist structural rigidity; the nature of z* and the model parameters.

The pharmacophoric model can be used in screening of new compounds for potential muscarinic activity in the following way a. the new structure is optimized to determine its low energy conformers; b. these conformers are examined for the proper arrangement of the pharmacophoric elements. Alternatively the new structure can be forced into the pharmacophoric conformation by using one of the induced fit routines. The resulting conformation is then compared to the low energy conformation of the same structure.

Application of these procedures produced a reliable answer in the cases examined (Table #1). Albeit there is no way to predict whether muscarinic activity is manifested only by compounds conforming to this model, those that do fit are active as agonists.

The limitation of volume for the cationic head for muscarinic agonists is inferred from docking experiments of the relevant structures (as depicted in Table #1) into a molecular model of the transmembrane domain of m1 muscarinic receptor. Compounds larger than quinuclidine derivatives cannot be accommodated by the macromolecular binding site.

The compounds listed in Table #1 are divided into four groups. The first group includes several well known muscarinic agonists. Their structures are characterized by optimal pharmacophoric parameters. The second group includes agonists that display suboptimal pharmacophoric patterns and are therefore mainly partial agonists. Structures of the compounds in the third group deviate from the pharmacophoric pattern for muscarinic activity, defined by the previous groups. These compounds are therefore either antagonists or devoid of muscarinic activity. Group four lists some of the potential muscarinic agonist based on their pharmacophoric parameters.

BIOLOGICAL TESTING

Test 1. Isolated Guinea-pig ileum preparation

Compounds of the invention were tested for their agonistic and antagonistic activities in the guinea-pig ileum preparation (method used as described by Fisher et al., J. Pharm. Exp. Therap. 257: 392–403 (1991). Table 2 summarizes the results obtained with some of the compounds.

Test 2: Binding to muscarinic receptors in the brain. Competition with [$^3$H]QNB, [$^3$H]NMS and [$^3$H]OXO-M in membranes prepared from rat cortex and cerebellum Rat cerebral cortex and cerebellar membrane preparations, using the ligands [$^3$H]NMS, [$^3$H]Pirenzepine and [$^3$H]oxotremorine-M were used for evaluating the new compounds. The ability of compounds to displace [$^3$H]oxotremorine-M {[$^3$H]OXO-M} binding provided a measure of affinity for the high affinity agonist state of the receptor. The ratio of the Ki values for the displacement of [$^3$H]NMS or [$^3$H]QNB and [$^3$H]OXO-M is used in the literature to predict efficacy. Ratios greater than 100 are associated with full agonists; antagonists give ratios close to unity and intermediate values indicate partial agonists (Orlek et al., J. Med. Chem. 34:2726, 1991).

The Ki values of the tested compounds for competing with [$^3$H]QNB binding are summarized in Table 3.

The rank order of the new drugs in competing with [$^3$H]NMS binding in cerebral cortex membranes was as follows:

AF102B>AF160(Des)≧AF185≧AF182=AF177=AF160>>AF179>>AF183.

The rank order of the new drugs in competing with [$^3$H]NMS binding in cerebellar membranes was as follows:

AF102B>AF160(Des)≧AF185≧AF160≧AF177≧AF179≧AF182>>AF183.

AF160(Des) and AF185 exhibited the highest potencies in both preparations among the group of the congeners of AF160.

The low affinities exhibited by the congeners of AF160 do not necessarily mean that the efficacies of these compounds are weak. For example, CCh, which also exhibits poor displacement potency, is known to be as efficacious as acetylcholine in activating the second messenger system, as well as the physiological responses mediated via muscarinic receptors in numerous preparations. In fact, AF160 was more efficacious than AF102B in activating PI turnover in cerebral cortex (vide infra). The new compounds were also studied in a [$^3$H]PZ competition assay using rat cerebral cortex membranes (Tables 3). AF160(Des) exhibited the highest affinity among the group of AF160 and its congeners in competing with [$^3$H]PZ binding to rat cerebral cortex membranes. Within the group of AF160 and its congeners, AF160 itself was the only compound which exhibited two-site competition curves with [$^3$H]PZ in rat cerebral cortex. This is in contrast with AF102B competition assays which typically yield mass-action curves. These observations may suggest some differences between recognition of rat cortex M1 receptors by AF102B and AF160 and its congeners.

The calculated ratios of $Ki^{PZ}/Ki^{NMS}$ (Table 3) are a commonly used indication for M1 selectivity of muscarinic ligands, lower ratios being indicative of better M1 selectivity. The group of AF160 and its congeners clearly exhibit low $Ki^{PZ}/Ki^{QNB}$ ratios. These findings indicate that such compounds may be selective M1 ligands for brain muscarinic receptors. the new compounds were studied in a competition assay with the labeled, non-selective muscarinic agonist, [$^3$H]OXO-M, employing rat cerebral cortex membranes (Table 4). The rank order among the drugs exhibiting single-site mass-action competition curves (group A in Table 4) was as follows:

AF102B>AF179≧AF160>>AF177=AF182>>AF183.

The potent agonistic character of AF179 and AF160 is also reflected in their relatively large $Ki^{NMS}/Ki^{OXO-M}$ values (Table 4).

AF160(Des) and AF185 were the only drugs tested whose competition curves (using [$^3$H]OXO-M and rat cerebral cortex membranes) did not exhibit single-site mass-action curves (Table 4). The extremely potent competition of these drugs with a sub-fraction of receptors labeled by [$^3$H]OXO-M in rat cerebral cortex membranes may indicate that these drugs are highly subtype selective. Thus, the calculated ratios of $Ki^{NMS}/K_H^{OXO-M}$ (Table 4) may indicate that AF160(Des) is a potent agonist for a subset of rat cerebral cortex muscarinic receptors, compared with the other congeners of the AF160 group and with AF102B itself. Surprisingly, AF160(Des) shows different kinetics as compared with standard agonists like carbachol pilocarpine, AF102B or AF160 (two sites curve during 30 rain assay period and I site curve at 60 rain incubation). This indicates that the kinetics of this compound with muscarinic receptors differ from other compounds.

The rat cerebellum is relatively homogeneous with respect to the mAChR subtypes expressed (mostly M2) whereas the cortex contains a mixed population of M1, M2 and M3 receptors. AF102B exhibited similar potencies in competing with [$^3$H]OXO-M binding in both preparations. In contrast, AF160(Des) and AF185 exhibited higher potencies in the cortex vs. the cerebellar membranes; this was reflected as two-site competition curves only ill the cortex membranes (Table 4).

Test No. 3

Second messenger activations in brain slices and in cell cultures

In a procedure for measuring the efficacy of the tested compounds as agonists on the M1 muscarinic receptors, brain slices from rat cortex (200 μM cubes) are prepared. For phosphoinositides (PI) turnover assay, these brain slices are loaded with [$^3$H]inositol (4uCi/ml) by incubating them in Krebs balanced salt solution containing the labeled ligand for 1 h at 37° C. under oxygenation. After washings, 50 ul aliquots are added to each tube containing 10mM LiCl in fresh Krebs solution with or without the tested compound. Following incubation for 20 min at 37° C., the reaction is terminated and labeled products are separated on AG-1-X8 columns as described by Berridge (Biochem. J. 258, 849–858, 1983). Partial agonists, according to the compound tested, produced a less than 80% activation of PI turnover as compared with CCh (a full agonist). Thus for example, AF160 caused a significant elevation in IP$_3$ (1.6 fold). In comparison to CCh, AF160 was a partial agonist with an efficacy of 50% of the reference compound. AF160(Des) was also active, although to a lesser extent than AF160. AF102B as another M1 agonist was less active than AF160.

Cell cultures enriched in one subpopulation of muscarinic receptors are used to evaluate second messenger activations by the tested compounds. For PI turnover studies the method of Berridge (Biochem. J. 258:849–858, 1983) is used; for arachidonic acid mobilization studies cells are labeled for 16h with 0.2uCi/ml of tritiated-arachidonic acid in original growth media. Prior to assay, cells are washed a total of six times with serum-free DME supplemented with HEPES (20 mM) and bovine serum albumin (1 mg/ml). Following the washing procedure, 0.5 ml of the same medium are added with ensuing addition of the rested ligands. Assays are terminated by transferring the media to Eppendorf tubes and centrifuging for 10 min at 6000 g. Radioactivity in supernatants is counted and presented as dpm tritiated-arachidonic acid released per well. Cyclic AMP accumulation in intact cells is evaluated according to the method of Pinkas-Kramarski et al, Neurosci. Lett. 108:335–340, 1990, whereas adenylyl cylase activity in isolated membranes is determined according to Johnson and Salomon (Methods in Enzymology Vol 195. R. A. Johnson and J. D. Corbin, eds. Academic Press, pp 3–21, 1991).

Compounds of Formulae I–IX with a maximal rate of PI turnover and/or arachidonic acid mobilization (but no significant activation of adenylyl cyclase) higher than 25% are preferred. Some examples for such activity can be found in AF102B, AF150(S), AF150, AF151, AF151(S), AF160, AF160(Des), AF178, AF179, AF180, AF185. These compounds are capable of activating M1 muscarinic receptors. However, unlike acetylcholine, CCh, oxotremorine-M and other classical full agonists, these compounds are inducing selective activation of distinct signalling via M1 (or M3) muscarinic receptors. In particular, the selective activation by muscarinic agonists of PI hydrolysis without (or with minimal) activation of cAMP accumulation is the general pattern of activity of the new compounds. These observations may imply induction of the M1 muscarinic receptor-coupling to distinct G-proteins by these selective muscarinic ligands. Thus in addition to the activation of the M1 receptors, these compounds are also selective at the level of distinct secondary messengers. This concept of select activation of only distinct G-proteins via the same muscarinic receptor using selective muscarinic ligands was recently described by the inventors under the concept of ligand-selective signaling employing CHO cells transfected with the rat m1AChR (Fisher et al. Biorganic & Medicinal Chem. Lett. 2:839–844, 1992) and in a neuronal type cell line, e.g. PC12M1 cell line (Soc. Neuroci. Abs. Nov. 1993). The possible relevance of this signaling pathway for the development of cholinergic replacement therapy for Alzheimer's disease (AD) is evident in view of findings on elevated Gs α-subunits levels in AD patients and aged brains (Harrison et al., Mol. Brain Res. 10:71, 1991; Young et al., Dev. Brain Res., 61:243, 1991). Thus compounds from the present invention can be important for the treatment of Alzheimer's disease.

Activation of M1 receptors by agonists can lead to synergistic effects with nerve growth factor (NGF) in certain cell cultures enriched with M1 receptors, e.g. PC12 (rat pheochromocytoma cells) transfected with the rat m1AChR (PC12M1 cells)(Pinkas-Kramarski et al, J. Neurochem. 59:2158–2166, 1992). According to another aspect of the invention, compounds of Formulae I-IX with a maximal rate of PI turnover higher than 25% can synergize the neurite outgrowth produced by NGF. Those compounds, which in in sharp contrast to oxotremorine or CCh, do not promote neurite-outgrowth in the absence of NGF, are preferred, since then no axonal growth would take place uncontrollably. Moreover, a favorable drug candidate for the treatment of Alzheimer's disease, for example, would induce neuritogenesis only under strict control of locally synthesized and released growth factors, such as NGF, brain-derived nerve factor (BDNF), NT-3 etc. Some examples for such a unique activity can be found in compounds like AF150(S), AF151(S), AF160, AF160(Des) which are at least 5 fold more potent than AF102B in synergizing NGF-induced neurite outgrowth. Neurites extended following a combined treatment with NGF and these new compounds were stable for long periods in culture. Hence, it can be assumed that the signaling pathway(s) employed by these compounds for induction of neurite outgrowth are not desensitizing rapidly. This is very reminiscent of NGF itself, which induces very stable and long-lasting neurite-promoting effects in PC12 cells, as well as in primary cultures of sympathetic neurons. It should be noted, however, that old untreated cultures of the tested cells were deteriorated, and contained many dead cells, which were detaching from the plate surface. Surprisingly, the cell death phenomena were smaller in cultures which were treated previously with a combination of the novel compounds and NGF. It is well known that NGF rescues PC12 cells from programmed cell death (e.g., Rukenstein et al., J. Neuroscience 11:2552–2563, 1991). Therefore, these observations can indicate that similar survival-promoting responses are mediated by compounds from the present invention. All these attributes are adding further value to the compounds as potential treatments for Alzheimer's disease patients.

In a further aspect of the invention, compounds of Formula I–IX, in particular those showing selective M1 agonistic activity can be beneficial not only in the treatment of AD, but in its prevention. This can be deduced from recent publications which showed that M1 receptor activation by muscarinic agonists leads to secretion of the beta-amyloid precursor protein (Nitch et al, Science 258:304,1992; Buxbaum et al, PNAS US 89:10075, 1992; Lahiri et al, Blochem. Int. 28:853, 1992). Those compounds from formulas I–IX which show a significant release (>15%) of the beta-amyloid precursor protein in PC12M1 cells for example (e.g., the content of beta-amyloid precursor protein is decreased in the cells) are preferable. Surprisingly, the release of the beta-amyloid precursor protein is more prominent in cultures which were pretreated with a combination of the novel compounds and NGF.

Test No. 4 Pharmacological and toxicological profiles

The study was carried out by observing the animals after iv or oral (mice) or oral (intra gastric for rats) administration of 3–6 dose levels of each substance.

Results are summarized in Table 5.

At different time intervals post-administration (10, 20, 30, 45, 60, 120, 240 min and 24 hr) animals were subjected to detailed observations of changes in general behavior, reflexes and autonomic effects. Mortality was recorded at 24 hr post administration of the test compounds. Body temperature in rats was measured using Tele-Thermometer (Model 46 TUC). The various pharmacological and behavioral parameters included: salivation, redness around the nose and mouth, chromodacryorrhea, sedation, ataxia, cyanosis, tremors, convulsions, hypothermia, opisthotonos, respiratory distress, diarrhea, gnowing, piloerection, mortality, changes in pupil diameter, rotarod, hypo- or hyperactivity and vocalization.

Some of the tested compounds are non-toxic up to 500 mg/kg (p.o., mice & rats).

AF160 is a relatively potent muscarinic agonist being more central than peripheral (e.g. hypothermia vs salivation), and less toxic at least 5 times when compared with AF102B. A remarkable finding in this compound was lack of tremors up to the highest tested dose (500 mg/kg, po) and some tremors in mice at doses >125 mg/kg, p.o. A similar pattern was detected in the methyl analog of AF160, namely AF178, where no tremors were detected in both mice and rats up to 500 mg/kg, p.o. Mice are more sensitive to this compound than rats, as peripheral and central side effects occur at lower doses.

AF160 in rats was found to be a potent agonist. Signs were apparent at a dose as low as 25 mg/kg. $ED_{50}$ values were obtained for hypothermia and gnawing. The extent and severity of symptoms were dose related. The hypothermic effect was long lasting, longer than 4 hr.

Four aspects are remarkable in AF160:
1. Apparently the compound is more CNS active than PNS active (e.g. hypothermia occurs at lower dose than salivation).
2. There is a CNS selectivity since not all CNS effects are observed (e.g. hypothermia vs lack of tremors).
3. The duration of the observed effects is long.
4. No mortality in mice and rats was observed at the highest dose level, 500 mg/kg.

AF160(Des) in rats

Salivation, hypothermia and diarrhea wre observed in one out of four animals 45 min after the administration of 125 mg/kg. Increasing the dose to 500 mg/kg the number of animals per group exhibiting these symptoms increased and in addition piloerection and sedation became distinct. The hypothermic effect was not dose-related. No other central or autonomic effects were produced by this compound. The compound is relatively inactive with regard to cholinergic side-effects.

In case of AF160(Des) side effects are elicited at doses >246 mg/kg, p.o., in rats.

AF160(Des) in mice

Signs as lacrimation, diarrhea and mydriasis were observed after the administration of 240 m/kg of AF160(Des). At higher doses and up to 1000 mg/kg, additional symptoms such as salivation, sedation and hypothermia were apparent. The extent and severity of most of the symptoms (except for lacrimation) were dose related. No mortality was observed even at the highest dose level, 1000 mg/kg. Topical application of 1 mg (threshold amount) of AF160(Des) into the eye produced mydriasis within 15 min. In contrast, atropine used as a reference drug for its known local mydriatic effect, produced mydriais within 45 min by as low as $4\times10^{-5}$mg. This result clearly shows that AF160(Des) induced-mydriasis is central in origin.

AF163 in rats

At the dose range between 50 to 400 mg/kg, salivation and redness around the nose and mouth were the only effects produced by this compound. These effects were of short onset (10 min) and short duration (20 min). Wherase the number of animals exhibiting salivation was dose related, redness around the nose was found only in one animal at signel dose level of 100 mg/kg. In conclusion, only autonomic effects were observed after po administration of this compound in rats.

AF163 in mice

Except of vocalization observed in one animal at the highest dose tested (400 mg/kg), this compound was devoid of any other overt effects. No overt peripheral & central side-effects were detected with AF163, in mice, up to the highest dose tested (400 mg/kg, p.o.).

AF163 can be considered a prodrug for AF160 in a similar way as the dithio analog of RS86 (see Bolliger et al, In: Alzheimer's and Parkinson's Disease; Strategies in R&D, eds. Fisher et al, Plenum Press, pp. 585, 1986).

AF177 in mice

Hypothermia, hypoactivity and tremors were observed 10 min after the administration of 31 mg/kg. Increasing the dose to 62 mg/kg, the number of symptoms increased. Sedation, ataxia, Straub-taill and falling from the rotarod were observed 20 min after administration in 4/4 mice. Mortality of 1/4 mice occurred 30 min after administration. When increasing the dose to 125, 250 and 500 mg/kg salivation, convulsions and mortality of 4/4 mice were also observed but the onset and the duration of the symptoms were harder from dose to dose. Calculated $ED_{50}$ values show that AF177 possess central effects mostly. AF177 can be considered a prodrug for a centrally active and potent muscarinic agonist.

AF178 in mice

Decreased motor activity, salivation, lacrimation and diarrhea were seen up to one hour after administration of 60 mg/kg. Increasing the dose to 500 mg/kg resulted in additional symptoms such as respiratory distress, decrease in the performance on the rotarod, tremors and mydriasis. The extent and severity of most of the symptoms were dose related.

In general, increasing the doses prolonged the activity. For example: diarrhea, tremors, mydiasis etc. lasted approximately 4 hours. It is worth mentioning that at 500 mg/kg one animal exhibited palpitation within 20 min after the administration, lasting for 10 min. Even though a dose of 500 mg/kg produced profound toxicological symptoms, nor mortality was recorded. Thus the estimated $LD_{50}$ would be at a dose higher than 500 mg/kg.

AF178 in rats

Salivation was the only overt sign following the administration of 62.5 mg/kg of AF178. Increasing the dose to 125 mg/kg more signs were apparent such as chromodacryorrea, hypothermia, diarrhea and gnowing. The extent and severity of those symptoms were increased with the dose. Respiratory distress was apparent only in one animal at a dose of 500 mg/kg, 5 min post injection. The compound can possess relatively broad safety margin.

AF178 in rats

Salivation was the only symptom produced by 125 mg/kg of AF180. It became evident within 20 min after administration and lasted for 40 min. Further increase the dose to 500 mg/kg increased the duration of the salivation to 230 min. At this dose level, hypothermia was also recorded in three animals 15 to 240 min post injection. No other central or autonomic effects were observed at this dose level.

AF180 in mice

Hypothermia and mydriasis were observed 20 min after the administration of 125 mg/kg. Increasing the dose to 500 mg/kg, the number of animals per group exhibiting these symptoms increased, and in addition salivation, lacrimation and sedation became distinct. Furthermore the duration of these symptoms was greater than 1.5 hr after administration of 500mg/kg. No other central or autonomic effects were produced by this compound. Topical application of 0.02 mg (threshold amount) of AF180 into the eye also produced mydriasis. This result indicate that the mydriatic effect of AF180 may be triggered by peripheral mechanisms.

Test No 5

The effects of AF134 in naive rats

The effects of AF134 on memory and learning ability was evaluated in a step-through passive avoidance task, in naive rats. The behavioral paradigm and instrumentation is as described in Fisher et al. Neurosci. Lett. 102:325 (1989). Four groups (20 rats/group) of naive male Sprague-Dawley rats, 200–300 gr, 3–4 months old (Charles River Breeding, UK) were treated with one of the following doses of AF134: 1, 5, 10 mg/kg, intraperitoneal (ip) and one group received saline (1 ml/kg, ip).

In AF134-treated rats no significant differences were found between the retention latency of the pre-shock treated rats in which the compound was injected 30 min before the shock and that of post-shock treated rats (in which the compound was injected 60 min after the shock).

In another experimental paradigm AF134 was compared with scopolamine (an antimuscarinic compound) in an 8-arm radial arm-maze in naive rats (behavioral pardigin and instrumentation as described in Fisher et al. Neurosci. Lett. 102:325, 1989). A group of 14 naive rats was treated with scopolamine (0.2 mg/kg,ip) or saline (1ml/kg, ip) 20 min before running the maze. All arms were baited. Each rat received both treatments with three days interval between treatments. (Ten days of training were followed by ten days of testing). The same experiment in the same rts was repeated with AF134 (5 mg/kg, ip) versus saline (1 ml/kg, ip). Scopolamine showed, as expected, a typical anticholinergic "amnesic" effect at the dose used. However, AF134 did not cause any change in the behaviour of the rats.

AF134 which has antagonistic activity on the M1 (based on binding studies) and M3 muscarinic receptors (based on guinea-pig ileum preparation) is not producing impairment of cognitive effects and thus may be useful in the treatment of motion sickness, Pakinson's disease, mixed Parkinson's and Alzheimer's disease, manic-depression, human head injury and in a variety of peripheral disorders in the treatment of acute rhinitis, peptic ulcer and asthma.

Test No 6

AF160 and AF102B - Radial Arm Maze

In the present work we have investigated the potential beneficial effect of doses of AF160 (3 and 5 mg/kg, p.o.) and AF102B (3 mg/kg, p.o.) in reversing memory deficits of AF64A-injected rats (1.5 nmole/2 µl/side). This animal models mimics to a certain extent the cholinergic hypofunction is SDAT. (Fisher et al, J. Pharmacol. Expl. Therap. 257:392–403, 1991). 80 Male Sprague-Dawley rats, 4–6 months old (340–580 gr) were used in this study. The time interval between operation and behavioral testing was 2–3 months. One week before starting the behavioral test, rats were transferred to individual cages and were food restricted until reaching approximately 85 % of their free feeding weight. Then rats received 5–6 pieces of Altromin (15 gr) per day in order to keep their body weight in a steady state. Rats had free access to water. The room was illuminated 12 hr a day (6:00–18:00) and behavioral testing was carried our during the morning.

Behavioral Testing

40 AF64A and 40 saline-injected rats were randomly subdivided into four subgroups and were assigned to AF160 3 mg/kg, AF160 5 mg/kg, AF102B 3 mg/kg (10 ml/kg, p.o.) and DDW.

During the first two days of behavioral testing, rats were trained according to the 8-out of 8 RAM-baiting-procedure, in order to familiarize them with the maze and the reinforcing pellets (precision 45 rag).

At this phase, rats were placed in the central arena and were allowed free access to all 8 baited arms. Each session was terminated when all eight pellets had been collected or at the end of 15 min, whichever came first.

During the third and fourth days pellets were placed only at the end of the arms. Otherwise the other procedures were the same as in pretraining.

Testing period was carried out during the second week of the experiment. During that time AF160, AF102B or DDW (used as control) were administered once a day, for five days, 60 min before testing.

Data analysis

All monvements within the maze were recorded, elapsed time as well as correct and incorrect responses. In order to evaluate the effect of AF160 or AF102B during the testing period compared to the training period which used as a baseline performance, a 3-way ANOVA (2×4×2) with a repeated variable (Blocks of training or testing days) and two non-repeated variables (Injection-AF64A/Saline and Treatment-various doses of AF160 and AF102B or DDW) was made. Post-hoc comparisons were completed using simple main effects' contrasts.

Results

Correct choices out of 8 visited

A significant interaction between groups x treatment x weeks was found [F(2/48)=3.95; P<0.025]. More specifically, during both training and drug administration period AF64A-injected rats made significantly less correct choices than saline-injected rats (P <0.001). Both drugs, AF102B (3 mg/kg) and AF160 (3 mg/kg) improved the performance of AF64A-injected rats during the second week compared to training days (P <0.001, respectively). During the second week both groups, AF160 (3 mg/kg) and AF102B (3 mg/kg) reached the same level of performance which was significantly higher than that of the AF64A injected rats treated with water (P<0.05). AF160 5 mg/kg had no significant effect on this parameter.

Referring to saline-injected rats the performance of rats treated with water improved (5%) during the second week compared to the first week (P<0.01). Similarly an improvement (7.5%) was also found in rats treated with AF160 (3 mg/kg) (P <0.001). AF102B (3 mg/kg) had no effect on this parameter in saline-injected rats.

Total errors

A significant interaction was found between groups x treatments x weeks [F(3/64)=3.49; P<0.025]. In both weeks the number of errors of AF64A-injected rats was significantly higher than that of saline injected rats (P<0.001). The number of errors of all four groups of AF64A-injected rats significantly decreased in the second week compared to the first week: AF64A+water-20% (P<0.01), AF64A+AF160-3 mg/kg-16% (P<0.001), AF64A+AF160-5 mg/kg-15% (P<0.02) and AF64A+AF102B-3 mg/kg-30% (P<0.001). Although all four groups improved their performace, only that of AF102B- 3 mg/kg was higher than the performance of the AF64A+water group. In saline-injected rats, AF160-3 and 5 mg/kg significantly improved the performance in the second week compared to the first week (P<0.01, P<0.001, respectively). AF102B-3 mg/kg produced a deterioration in performance and this group made more errors in the second week compared to the first week (P<0.001).

Total time:

A significant interaction was found between groups x treatment x weeks [F(2/48)=3.29; P<0.05).

An improvement in time was found in AF64A-injected subgroups except AF64A+AF160- 5 mg/kg: AF64A+water-31% (P<0.01), AF64A +AF160-3 mg/kg-(47 %) (P<0.001 ) and AF64A+AF102B 3 mg/kg-(21%) (P<0.01). In saline-injected rats a significant effect of improvement in time was found in saline+water-(54%) (P<0.001) and saline+AF160 3 mg/kg-(37%) (P<0.001). AF102B had no effect on saline-injected rats on this parameter, maybe because of a "floor effect". AF160-5 mg/kg did not affect significantly the saline-injected rats performance although a tendency for improvement can be observed.

In conclusion

1. Rats injected with AF64A (1.5 nnmole/2 μl/side) showed a significant impairment in the parameters of correct choices, number of errors and total time compared to saline-injected rats.
2. AF160 (3 mg/kg) significantly improved the performance of AF64A-injected rats (compared to placebo treatment) in the parameters of correct choices and total time. A higher dose of 5 mg/kg was found effective only in the parameter of number of errors compared to baseline (but not to placebo).

AF160(Des)—Morris Water Maze (MWM) task

The objective of this study was to evaluate the ability of the test material AF160(Des) to reverse cognitive impairments in AF64A-injected rats using the MWM task according to the method by Fisher et al, J. Pharmacol. Exptl. Therap. 257: 392–403, 1991.

AF160(Des) was tested using two doses: 1 and 3 mg/kg p.o.

38 AF64A (3 nmol/2 ul/side)- and 42 Saline-injected rats were randomly subdivided into 4 subgroups and were assigned to the different doses of and AF160(Des) (1 and 3 mg/kg, p.o.) or DDW (10 ml/kg, p.o.). The drug was administered once a day for 5 days, 60 min before testing.

No consistent side-effects were observed during behavioral testing. The following results were obtained:

1. An injection of AF64A (3 nmol/2ul/side) resulted in a significant impairment in performance, as indicated by both parameters escape latency and path length.
2. AF160(Des)-3mg/kg improved the performance of both AF64A and saline-injected rats on the third block of training. The positive effect suggests using various doses of that compound in the future in order to test its possible beneficial effects on learning and memory deficits.

TABLE 1

Pharmacophoric parameters for muscarinic agonists

| Agonist | Selectivity | r-X[1] (A) | r-Q* (A) | X*—Q* (A) | r-X*—Q*—Z* |
|---|---|---|---|---|---|
| group 1 | | | | | |
| ACh | M2 > M1 | 6.40 | 8.44 | 2.40 | −86 (═O) |
| Dioxolane | M2 > M1 | 6.51 | 8.71 | 2.42 | −85 (—O) |
| Muscarine | Mw > M1 | 6.50 | 8.53 | 2.44 | −75 (—O) |
| Methylfur-methide | M1 > M2 | 6.40 | 8.54 | 2.43 | −59 (═C) |
| Oxatholane | M1 > M2 | 6.55 | 8.90 | 2.43 | −25 (—S) |
| group 2 | | | | | |
| AF102B | M1 > M2 | 5.93 | 8.24 | 2.45 | −173 |
| AF150 | M1 > M2 | 5.78 | 7.91 | 2.45 | −118 |
| AF151 | M1 > M2 | 5.82 | 8.20 | 2.45 | −170 |
| AF150(S) | M1 > M2 | 5.72 | 8.35 | 2.81 | −84 |
| AF151(S) | M1 > M2 | 5.88 | 8.15 | 2.38 | −177 |
| AF160 | M1 > M2 | 5.80 | 8.26 | 2.72 | −96 |
| AF160 (Des) | M1 > M2 | 5.78 | 8.26 | 2.70 | −95 |
| group 3 | | | | | |
| AF133 | | 5.98 | 8.33 | 2.96 | 34 |
| AF134 | | 6.00 | 8.58 | 2.62 | 9 |
| AF168 | | 6.69 | 9.10 | 2.72 | −44 |
| AF172 | | 5.71 | 9.64 | 4.00 | −101 |
| group 4 | | | | | |

TABLE 1-continued

Pharmacophoric parameters for muscarinic agonists

| Agonist | Selectivity | r-X$^t$ (A) | r-Q* (A) | X*—Q* (A) | r-X*—Q*—Z* |
|---|---|---|---|---|---|
| AF170 | | 6.07 | 8.62 | 3.01 | −60 |
| A202 | | 5.78 | 8.10 | 2.42 | −170 |
| AF210 | | 5.89 | 8.20 | 2.43 | −170 |
| AF215 | | 5.94 | 7.93 | 2.44 | −108 |
| AF216 | | 5.72 | 8.32 | 2.84 | −96 |
| AF260 | | 5.75 | 8.02 | 2.45 | −132 |
| AF270 | | 5.79 | 8.27 | 2.73 | −93 |

TABLE 2

The effect of various putative cholinergic compounds on the guinea-pig ileum preparation

| Tested compound | EC$_{50}$ μM | Remarks |
|---|---|---|
| AF102B* | 3.5 | Partial Agonist |
| AF134 | | Antagonist at 6 μM |
| AF151(S) | 7.3 | Full Agonist |
| AF160 | 3.2 | Full Agonist |
| AF160(Des) | | Partial Agonist at 0.1 mM maximal contraction of 80% of carbachol |
| AF177 | | Weak antagonist at 0.25 mM; |
| AF178 | 100 | Partial Agonist (80% of ACh) |
| AF179 | 100 | Partial Agonist (80% of ACh) |
| AF180 | 100 | Partial Agonist (80% of ACh) |
| AF182 | | Antagonist at 0.1 mM; Full antagonist at 0.2 mM |

*cis-2-methylspiro (1,3-oxathiolane-5,3')quinuclidine (U.S. Pat No. 4,855, 29)
AF134 behaved as a muscarinic antagonist in the guinea-pig ileum preparation. Surprisingly, AF134 inhibited AF102B-induced contractions better than it blocked acetylcholine (ACh)-induced contractions. Thus if the contraction induced by AF102B in this preparation are mediated mainly through M3 receptors, AF134 appears to be a selective M3 antagonist in this preparation.
*Weak antagonist (at 0.1 mM) for ACh-induced contraction.

TABLE 3

Competition of tested compounds with [$^3$H]PZ, [$^3$H]NMS or [$^3$H]QNB (rat cortex) and [$^3$H]QNB or [$^3$H]NMS (cerebellum), respectively.

| | Cortex | | | | | | Cerebellum | | | |
|---|---|---|---|---|---|---|---|---|---|---|
| | [$^3$H]PZ | | [$^3$H]QNB | | [3H]-NMS | | [$^3$H]QNB | | [$^3$H]NMS | |
| Compound | K$_{H'}$(%) uM | K$_L$(%) uM | K$_H$(%) uM | K$_L$(%) uM | K$_H$(%) uM | KL uM | K$_H$(%) uM | K$_L$ uM | K$_H$(%) Um | K$_L$ |
| Carbachol | .06(38) | 18.6 | 6.8(18) | 980 | .1(41) | 11 | 1.5(54) | 52 | .02(56) | 6 |
| Oxotremorine | | | | 2.4 | | | | .8 | | |
| McN—A-343 | | | | 7.9 | | | | 24.4 | | |
| AF102B | | 1 | | 7.1 | | 1.1, 1.5 | | 18.1 | | 1.4, 0.4 |
| AF133 | | 2.7 | | | | | | 5.1 | | |
| AF134 | | .13 | | | | | | 3.8 | | |
| AF151(S) | 0.75(11) | 20 | 24(44) | 459 | | | | 45 | | |
| AF160 | 1.4(34) | 19 | | 58 | .45(31) | 12 | | 61 | 0.56 (46) | 19 |
| AF160(Des) | 1.3(36) | 9 | | 40 | | 7 | 5(36) | 86 | | 2.4 |
| AF178 | 17(58) | 90 | | | | | | 200 | | |
| AF180 | | 5.4 | | | | | | 350 | | |
| AF177 | .06(10) | 7 | | | .1(14) | 13 | | | | 20 |
| AF182 | .06(27) | 8.3 | | | .12(23) | 9.2 | | | | 21 |
| AF183 | | | .06(14) | 100 | | 260 | | | | 310 |
| AF185 | | | | 4.8 | | 9 | | | | 7 |

TABLE 4

Competition with [$^3$H]OXO—M by congeners of AF160 and reference muscarinic agonists in rat cerebral cortex preparation.

| Compound | Ki (μM) | Ki$^{NMS}$/Ki$^{OXO—M}$ |
|---|---|---|
| A. mass action curves | | |
| CCh | 0.06 ± 0.005 (3) | 380 |
| Pilocarpine | 0.1 | |
| AF102B | 0.6 ± 0.2 (3) | 2.1 |
| AF160 | 1.8 ± 0.2 (3) | 9.4 |
| AF177 | 11 | 1.4 |
| AF179 | 1.3 ± 0.3 | 31 |
| AF182 | 14 | 1 |
| AF183 | >100 | ~1 |

TABLE 4-continued

|  |  | $K_H$ (μM) | %H | $K_L$ (μM) | $Ki^{NMS}/K_L^{OXO-M}$ |
|---|---|---|---|---|---|
| B. Two-site competition curves |  |  |  |  |  |
| AF160(Des) | Exp. 1 | 0.05 | 36% | 2.2 |  |
|  | Exp. 2 | 0.03 | 58% | 1.8 |  |
|  | Exp. 3 | 0.02 | 42% | 2.1 |  |
|  | mean(1–3) | 0.033 ± 0.007 (3) | 45 ± 6% | 2.0 ± 0.1 | 3.5 |
| AF185 | Exp. 1 | 0.04 | 53% | 49 | 0.18 |
|  | Exp. 2 | 0.01 | 18% | 3 | 3 |

Binding experiments were performed using washed rat cerebral cortex membranes in TRIS/$Mn^{2+}$ buffer for 30 min at 25° C. $Ki^{NMS}$ data are mean values from Table 3.
Data are from 1–4 experiments.
A. Data for drugs exhibiting mass-action competition curves with [$^3$H]OXO—M.
B. Data for drugs exhibiting two-site competition curves with [$^3$H]OXO—M.
Note: in the case of AF160(Des) and AF185 we observed mass-action curves in certain experiments.

TABLE 5

Pharmacological and toxicological profiles in mice and /or rats after oral (if not mentioned otherwise) administration of the tested compounds

| Examples | Dose mg/kg, po | Salivat. | Chr., rats Lac., mice | Sed. | Ata. | Cyan. | Trem. | Conv. | Hypo. | Mydria. | Res. | Diar | Gno. | Pilo | Mortality |
|---|---|---|---|---|---|---|---|---|---|---|---|---|---|---|---|
| AF133 | 50(iv) |  |  |  |  |  |  |  |  |  |  |  |  |  | 0/5 |
|  | 100 (iv) |  |  |  |  |  |  |  |  |  |  |  |  |  | 3/5 |
| mice | 200 (iv) |  |  |  |  |  |  |  |  |  |  |  |  |  | 5/5 |
|  | 400 |  |  |  |  |  |  |  |  |  |  |  |  |  | 1/5 |
| AF134 | 10(iv) |  |  |  |  |  |  |  |  |  |  |  |  |  | 0/5 |
|  | 25(iv) |  |  |  |  |  |  |  |  |  |  |  |  |  | 0/5 |
| mice | 50(iv) |  |  |  |  |  |  |  |  |  |  |  |  |  | 0/5 |
|  | 100(iv) |  |  |  |  |  | 4/5 |  |  |  | 2/5 |  |  |  | 3/5 |
|  | 100 |  |  |  |  |  |  |  |  |  |  |  |  |  | 0/5 |
|  | 200 |  |  |  |  |  |  |  |  |  | 1/5 |  |  |  | 0/5 |
| AF151 | 50 | 4/4 | 4/4 | 3/4 | 0/4 | 0/4 | 0/4 | 0/4 | 0/4 |  | 0/4 | 0/4 | 0/4 | 0/4 | 0/4 |
| (S) | 100 | 4/4 | 4/4 | 4/4 | 0/4 | 0/4 | 0/4 | 0/4 | 0/4 |  | 0/4 | 3/4 | 0/4 | 0/4 | 0/4 |
| rats | 200 | 4/4 | 4/4 | 4/4 | 2/4 | 1/4 | 1/4 | 1/4 | 0/4 |  | 1/4 | 4/4 | 0/4 | 0/4 | 1/4 |
|  | 500 | 4/4 | 4/4 | 4/4 | 4/4 | 4/4 | 4/4 | 4/4 | 0/4 |  | 2/4 | 4/4 | 0/4 | 0/4 | 2/4 |
| AF160 | 8 | 0/4 | 0/4 | 0/4 | 0/4 | 0/4 | 0/4 | 0/4 | NT |  | 0/4 | 0/4 | NT | NT | 0/4 |
|  | 16 | 0/4 | 1/4 | 0/4 | 0/4 | 0/4 | 0/4 | 0/4 |  |  | 0/4 | 1.4 |  |  | 0/4 |
| mice | 31 | 2/4 | 3/4 | 0/4 | 0/4 | 0/4 | 0/4 | 0/4 |  |  | 0/4 | 1/4 |  |  | 0/4 |
|  | 63 | 4/4 | 4/4 | 4/4 | 0/4 | 0/4 | 0/4 | 0/4 |  |  | 0/4 | 0/4 |  |  | 0/4 |
|  | 125 | 3/4 | 4/4 | 4/4 | 0/4 | 0/4 | 1/4 | 0/4 |  |  | 0/4 | 2/4 |  |  | 0/4 |
|  | 250 | 4/4 | 4/4 | 4/4 | 4/4 | 0/4 | 4/4 | 0/4 |  |  | 0/4 | 3/4 |  |  | 0/4 |
|  | 500 | 4/4 | 4/4 | 4/4 | 4/4 | 0/4 | 4/4 | 0/4 |  |  | 0/4 | 3/4 |  |  | 0.4 |
|  | 10 | 0/4 | 0/4 | 0/4 | 0/4 | 0/4 | 0/4 | 0/4 | 0/4 |  | 0/4 | 0/4 | 0/4 | 0/4 | 0/4 |
|  | 25 | 0/4 | 1/4 | 0/4 | 0/4 | 0/4 | 0/4 | 0/4 | 4/4 |  | 0/4 | 0/4 | 4/4 | 0/4 | 0/4 |
|  | 50 | 4/4 | 4/4 | 0/4 | 1/4 | 0/4 | 0/4 | 0/4 | 4/4 |  | 0/4 | 4/4 | 4/4 | 0/4 | 0/4 |
|  | 100 | 4/4 | 4/4 | 4/4 | 0/4 | 0/4 | 0/4 | 0/4 | 4/4 |  | 1/4 | 4/4 | 4/4 | 0/4 | 0/4 |
|  | 200 | 4/4 | 4/4 | 4/4 | 4/4 | 0/4 | 0/4 | 0/4 | 4/4 |  | 2/4 | 4/4 | 4/4 | 2/4 | 0/4 |
|  | 500 | 4/4 | 4/4 | 4/4 | 4/4 | 0/4 | 4/4 | 0/4 | 4/4 |  | 0/4 | 4/4 | 4/4 | 4/4 | 0/4 |
| AF160 | 1-63 | 0/4 | 0/4 | 0/4 | 0/4 | 0/4 | 0/4 | 0/4 | 0/4 |  | 0/4 | 0/4 | 0/4 | 0/4 | 0/4 |
| (Des) | 125 | 1/4 | 0/4 | 0/4 | 0/4 | 0/4 | 0/4 | 0/4 | 1/4 |  | 0/4 | 1/4 | 0/4 | 0/4 | 0/4 |
|  | 250 | 2/4 | 0/4 | 0/4 | 0/4 | 0/4 | 0/4 | 0/4 | 1/4 |  | 0/4 | 1/4 | 0/4 | 0/4 | 0/4 |
| rats | 500 | 3/4 | 0/4 | 4/4 | 0/4 | 0/4 | 0/4 | 0/4 | 0/4 |  | 0/4 | 3/4 | 0/4 | 1/4 | 0/4 |
| mice | 120 | 0/4 | 0/4 | 0/4 | 0/4 | 0/4 | 0/4 | 0/4 | 0/4 | 0/4 | 0/4 | 0/4 |  |  | 0/4 |
|  | 240 | 0/4 | 0/4 | 0/4 | 0/4 | 0/4 | 0/4 | 0/4 | 0/4 | 4/4 | 0/4 | 1/4 |  |  | 0/4 |
|  | 500 | 1/4 | 0/4 | 0/4 | 0/4 | 0/4 | 0/4 | 0/4 | 0/4 | 4/4 | 0/4 | 2/4 |  |  | 0/4 |
|  | 1000 | 2/4 | 0/4 | 1/4 | 0/4 | 0/4 | 0/4 | 0/4 | 4/4 | 3/4 | 0/4 | 3/4 |  |  | 0/4 |
| AF163 | 25 | 0/4 | 0/4 | 0/4 | 0/4 | 0/4 | 0/4 | 0/4 | NT |  | 0/4 | 0/4 | 0/4 | NT | NT | 0/4 |
| mice | 50 | 0/4 | 0/4 | 0/4 | 0/4 | 0/4 | 0/4 | 0/4 |  |  | 0/4 | 0/4 | 0/4 |  |  | 0/4 |
|  | 100 | 0/4 | 0/4 | 0/4 | 0/4 | 0/4 | 0/4 | 0/4 |  |  | 0/4 | 0/4 | 0/4 |  |  | 0/4 |
|  | 200 | 0/4 | 0/4 | 0/4 | 0/4 | 0/4 | 0/4 | 0/4 |  |  | 0/4 | 0/4 | 0/4 |  |  | 0/4 |
|  | 400 | 0/4 | 0/4 | 0/4 | 0/4 | 0/4 | 0/4 | 0/4 |  |  | 0/4 | 0/4 | 0/4 |  |  | 0/4 |
| rats | 50 | 0/4 | 0/4 | 0/4 | 0/4 | 0/4 | 0/4 | 0/4 | 0/4 |  | NT | 0/4 | 0/4 | 0/4 | 0/4 | 0/4 |
|  | 100 | 2/4 | 0/4 | 0/4 | 0/4 | 0/4 | 0/4 | 0/4 | 0/4 |  | NT | 0/4 | 0/4 | 0/4 | 0/4 | 0/4 |
|  | 200 | 4/4 | 0/4 | 0/4 | 0/4 | 0/4 | 0/4 | 0/4 | 0/4 |  | NT | 0/4 | 0/4 | 0/4 | 0/4 | 0/4 |
|  | 400 | 4/4 | 0/4 | 0/4 | 0/4 | 0/4 | 0/4 | 0/4 | 0/4 |  | NT | 0/4 | 0/4 | 0/4 | 0/4 | 0/4 |
| AF177 | 31 | 0/4 | 0/4 | 0/4 | 0/4 | 0/4 | 4/4 | 0/4 | 4/4 |  | 0/4 | 0/4 | 0/4 | NT | NT | 0/4 |
| mice* | 62 | 0/4 | 0/4 | 0/4 | 0/4 | 0/4 | 4/4 | 0/4 | 4/4 |  | 0/4 | 0/4 | 0/4 |  |  | 0/4 |
|  | 125 | 3/4 | 0/4 | 0/4 | 0/4 | 0/4 | 4/4 | 4/4 | 2/4 |  | 0/4 | 0/4 | 0/4 |  |  | 4/4 |
|  | 250 | 4/4 | 0/4 | 0/4 | 0/4 | 0/4 | 4/4 | 4/4 | 1/4 |  | 0/4 | 0/4 | 0/4 |  |  | 4/4 |
|  | 500 | 4/4 | 0/4 | 4/4 | 4/4 | 0/4 | 4/4 | 4/4 |  |  | 0/4 | 0/4 | 0/4 |  |  | 4/4 |
| AF178 | 30 | 0/4 | 0/4 | 0/4 | 0/4 | 0/4 | 0/4 | 0/4 | NT |  | 0/4 | 0/4 | 0/4 | NT | NT | 0/4 |
| mice | 40 | 1/4 | 2/4 | 0/4 | 0/4 | 0/4 | 0/4 | 0/4 |  |  | 0/4 | 0/4 | 4/4 |  |  | 0/4 |

TABLE 5-continued

Pharmacological and toxicological profiles in mice and /or rats after oral
(if not mentioned otherwise) administration of the tested compounds

| Examples | Dose mg/kg, po | Salivat. | Chr., rats Lac., mice | Sed. | Ata. | Cyan. | Trem. | Conv. | Hypo. | Mydria. | Res. | Diar | Gno. | Pilo | Mortality |
|---|---|---|---|---|---|---|---|---|---|---|---|---|---|---|---|
|  | 144 | 3/4 | 3/4 | 0/4 | 0/4 | 0/4 | 0/4 | 0/4 |  | 0/4 | 0/4 | 3/4 |  |  | 0/4 |
|  | 288 | 4/4 | 3/4 | 0/4 | 0/4 | 0/4 | 0/4 | 0/4 |  | 0/4 | 3/4 | 2/4 |  |  | 0/4 |
|  | 500 | 4/4 | 4/4 | 0/4 | 0/4 | 0/4 | 4/4 | 0/4 |  | 2/4 | 0/4 | 4/4 |  |  | 0/4 |
| rats | 63 | 1/4 | 0/4 | 0/4 | 0/4 | 0/4 | 0/4 | 0/4 | 0/4 | NT | 0/4 | 0/4 | 0/4 | 0/4 | 0/4 |
|  | 125 | 4/4 | 3/4 | 0/4 | 0/4 | 0/4 | 0/4 | 0/4 | 3/4 |  | 0/4 | 4/4 | 4/4 | 0/4 | 0/4 |
|  | 250 | 3/4 | 3/4 | 1/4 | 0/4 | 0/4 | 0/4 | 0/4 | 3/4 |  | 0/4 | 4/4 | 3/4 | 0/4 | 0/4 |
|  | 500 | 4/4 | 3/4 | 4/4 | 0/4 | 0/4 | 0/4 | 0/4 | 4/4 |  | 1/4 | 4/4 | 4/4 | 0/4 | 0/4 |
| AFI80 mice | 63 | 0/4 | 0/4 | 0/4 | 0/4 | 0/4 | 0/4 | 0/4 | NT | 0/4 | 0/4 | 0/4 | NT | NT | 0/4 |
|  | 125 | 0/4 | 0/4 | 0/4 | 0/4 | 0/4 | 0/4 | 0/4 |  | 2/4 | 0/4 | 0/4 |  |  | 0.4 |
|  | 250 | 3/4 | 0/4 | 0/4 | 0/4 | 0/4 | 0/4 | 0/4 |  | 3/4 | 0/4 | 0/4 |  |  | 0/4 |
|  | 500 | 4/4 | 3/4 | 3/4 | 0/4 | 0/4 | 0/4 | 0/4 |  | 4/4 | 0/4 | 0/4 |  |  | 0/4 |
| rats | 31 | 0/4 | 0/4 | 0/4 | 0/4 | 0/4 | 0/4 | 0/4 | 0/4 | NT | 0/4 | 0/4 | 0/4 | 0/4 | 0/4 |
|  | 62 | 0/4 | 0/4 | 0/4 | 0/4 | 0/4 | 0/4 | 0/4 | 0/4 |  | 0/4 | 0/4 | 0/4 | 0/4 | 0/4 |
|  | 125 | 1/4 | 0/4 | 0/4 | 0/4 | 0/4 | 0/4 | 0/4 | 0/4 |  | 0/4 | 0/4 | 0/4 | 0/4 | 0/4 |
|  | 250 | 2/4 | 0/4 | 0/4 | 0/4 | 0/4 | 0/4 | 0/4 | 4/4 |  | 0/4 | 0/4 | 0/4 | 0/4 | 0/4 |

Abbreviations Salivat. = salivation; Chr. = chromodacryorrhea; Sed. + desation; Ata. = ataxia; Cyan. = cyanosis; Trem. = tremors; Conv. + convulsions; Hypot. = hypothermia; Mydr. = mydriasis; Res. respiratory distress; Diar. = diarrhea; Gno. = gnowing; Pilo. + Piloerection.

While the present invention has been particularly described herein, with especial reference to exemplified and otherwise specified embodiments, persons skilled in the art will be aware that many variations and modifications may be made. The invention is accordingly not to be construed as restricted to such embodiments which have been particularly described, rather its concept, scope and spirit are to be understood having regard to the claims which follow.

We claim:

1. A compound having muscarinic activity and which is selected form the group consisting of:

1-methylpiperidine-4-spiro-5'-(3'-ethylhydantoin),
1-methylpiperidine-4-spiro-5'-(1'-acetylhydantoin),
piperidine-4-spiro-5'-(3'-ethylhydantoin),
1-methylpiperidine-4-spiro-5'-(3'-methylhydantoin),
piperidine-4-spiro-5'-(3'-methylhydantoin),
1-methylpiperidine-4-spiro-5'-(3'-propargylhydantoin),
1-methylpiperidine-4-spiro-5'-(3'-ethyl-4'-thiohydantoin),
1-methylpiperidine-4-spiro-5'-(4'-methylthio-3'-imidazoline-2'-thione),
1-methylpiperidine-4-spiro-5'-(2',4'-dithiohydantoin),
1-methylpiperidine-4-spiro-5'-(3'-ethyl-2',4'-dithiohydantoin),
1-methylpiperdine-4-spiro-5'-(4'-ethylthio-3'-imidazoline-2'-thione),
1-methylpiperidine-4-spiro-4'-(1'-ethyl-2'-ethylthio-2'-imidazoline-5'-thione),
1-methylpiperidine-4-spiro-5'-(2'-thiohydantoin),
1-methylpiperidine-4-spiro-5'-(2'-thio-4'-β-hydroxyethyliminohydantoin),
1-methylpiperidine-4-spiro-5'-(oxazolidine-2'-thione),
1-methylpiperidine-4-spiro-5'-(3'-ethyloxazolidine-2'-one),
1-methylpiperidine-4-spiro-4'-(3'ethyloxazolidine-2'-one),
1-methylpiperidine-4-spiro-4'-(2'-methyl-2'-thiazoline),
1-methylpiperidine-4-spiro-4'(5')-(2'-methyl-2'-imidazoline),
1-methylpiperidine-4-spiro-5'-(2'-methyl-2'-oxazoline-4'-one), and their pharmaceutically acceptable salts, quaternary compounds, enantiomers and racemates.

2. A compound according to claim 1, which is: 1-methylpiperidine-4-spiro-5'-(3'-ethylhydantoin).

3. A compound according to claim 1, which is: 1-methylpiperidine-4-spiro-5'-(1'-acetylhydantoin).

4. A compound according to claim 1, which is: piperidine-4-spiro-5'-(3'-ethylhydantoin).

5. A compound according to claim 1, which is: 1-methylpiperidine-4-spiro-5'-(3'-methylhydantoin).

6. A compound according to claim 1, which is: piperidine-4-spiro-5'-(3'-methylhydantoin).

7. A compound according to claim 1, which is: 1-methylpiperidine-4-spiro-5'-(3'-propargylhydantoin).

8. A compound according to claim 1, which is: 1-methylpiperidine-4-spiro-5'-(3'-ethyl-4'-thiohydantoin).

9. A compound according to claim 1, which is: 1-methylpiperidine-4-spiro-5'-(4'-methylthio-3'-imidazoline-2'-thione).

10. A compound according to claim 1, which is: 1-methylpiperidine-4-spiro-5'-(2',4'-dithiohydantoin).

11. A compound according to claim 1, which is: 1-methylpiperidine-4-spiro-5'-(3'-ethyl-2',4'-dithiohydantoin).

12. A compound according to claim 1, which is: 1-methylpiperidine-4-spiro-5'-(4'-ethylthio-3'-imidazoline-2'-thione).

13. A compound according to claim 1, which is: 1-methylpiperidine-4-spiro-4'-(1'-ethyl-2'-ethylthio-2'-imidazoline-5'-thione).

14. A compound according to claim 1, which is: 1-methylpiperidine-4-spiro-5'-(2'-thiohydantoin).

15. A compound according to claim 1, which is: 1-methylpiperidine-4-spiro-5'-(2'-thio-4'-β-hydroxyethyliminohydantoin).

16. A compound according to claim 1, which is: 1-methylpiperidine-4-spiro-5'-(oxazolidine-2'-thione).

17. A compound according to claim 1, which is: 1-methylpiperidine-4-spiro-5'-(3'-ethyloxazolidine-2'-one).

18. A compound according to claim 1, which is: 1-methylpiperidine-4-spiro-4'-(3'-ethyloxazolidine-2'-one).

19. A compound according to claim 1, which is:
1-methylpiperidine-4-spiro-4'-(2'-methyl-2'-thiazoline).

20. A compound according to claim 1, which is:
1-methylpiperidine-4-spiro-4'-(5')-(2'-methyl-2'-imidazoline).

21. A compound according to claim 1, which is:
1-methylpiperidine-4-spiro-5'-(2'-methyl-2'-oxazoline-4'-one).

22. A pharmaceutical composition for use in treating disease of the central and peripheral nervous system in mammals, which comprises an amount effective for use in treating said diseases, of a compound having muscarinic activity and which is selected from the group consisting of:

1-methylpiperidine-4-spiro-5'-(3'-ethylhydantoin),
1-methylpiperidine-4-spiro-5'-(1'-acetylhydantoin),
piperidine-4-spiro-5'-(3-ethylhydantoin),
1-methylpiperidine-4-spiro-5'-(3'-methylhydantoin),
piperidine-4-spiro-5'-(3'-methylhydantoin),
1-methylpiperidine-4-spiro-5'-(3'-propargylhydantoin),
1-methylpiperidine-4-spiro-5'-(3'-ethyl-4'-thiohydantoin),
1-methylpiperidine-4-spiro-5'-(4'-methylthio-3'-imidazoline-2'-thione),
1-methylpiperidine-4-spiro-5'-(2',4'-dithiohydantoin),
1-methylpiperidine-4-spiro-5'-(3'-ethyl-2',4'-dithiohydantoin),
1-methylpiperidine-4-spiro-5'-(4'-ethylthio-3'-imidazoline-2'-thione),
1-methylpiperidine-4-spiro-4'-(1'-ethyl-2'-ethylthio-2'-imidazoline-5'-thione),
1-methylpiperidine-4-spiro-5'-(2'-thiohydantoin),
1-methylpiperidine-4-spiro-5'-(2'-thio-4'-β-hydroxyethyliminohydantoin).
1-methylpiperidine-4-spiro-5'-(oxazolidine-2'-thione),
1-methylpiperidine-4-spiro-5'-(3'-ethyloxazolidine-2'-one),
1-methylpiperidine-4-spiro-4'-(3'-ethyloxazolidine-2'-one),
1-methylpiperidine-4-spiro-4'-(2'-methyl-2'-thiazoline),
1-methylpiperidine-4-spiro-4'(5')-(2'-methyl-2'-imidazoline),
1-methylpiperidine-4-spiro-5'-(2'-methyl-2'-oxazoline-4'-one), and their pharmaceutically acceptable salts, quaternary compounds, enantiomers and racemates.

23. A pharmaceutical composition according to claim 22, which is in a form suitable for oral, rectal, parenteral or transdermal administration, or for administration by insufflation or nasal spray.

24. A pharmaceutical composition according to claim 22, which is in a form suitable for transdermal administration and comprises as an additional component, a low molecular weight fatty acid.

25. A pharmaceutical composition according to claim 22, which is in unit dosage form.

26. A pharmaceutical composition according to claim 25, which comprises said compound in an amount in the range of about 0.5 to about 100 mg per unit dosage.

27. A method for treating diseases of the central or peripheral nervous system in mammals, which comprises administering to the mammal an amount effective for use in treating said diseases, of a compound having muscarinic activity and which is selected from the group consisting of:

1-methylpiperidine-4-spiro-5'-(3'-ethylhydantoin),
1-methylpiperidine-4-spiro-5'-(1'-acetylhydantoin),
piperidine-4-spiro-5'-(3'-ethylhydantoin),
1-methylpiperidine-4-spiro-5'-(3'-methylhydantoin),
piperidine-4-spiro-5'-(3'-methylhydantoin),
1-methylpiperidine-4-spiro-5'-(3'-propargylhydantoin),
1-methylpiperidine-4-spiro-5'-(3'-ethyl-4'-thiohydantoin),
1-methylpiperidine-4-spiro-5'-(4'-methylthio-3'-imidazoline-2'-thione),
1-methylpiperidine-4-spiro-5'-(2',4'-dithiohydantoin),
1-methylpiperidine-4-spiro-5'-(3'-ethyl-2',4'-dithiohydantoin),
1-methylpiperidine-4-spiro-5'-(4'-ethylthio-3'-imidazoline-2'-thione),
1-methylpiperidine-4-spiro-4'-(1'-ethyl-2'-ethylthio-2'-imidazoline-5'-thione),
1-methylpiperidine-4-spiro-5'-(2'-thiohydantoin),
1-methylpiperidine-4-spiro-5'-(2'-thio-4'-β-hydroxyethyliminohydantoin).
1-methylpiperidine-4-spiro-5'-(oxazolidine-2'-thione),
1-methylpiperidine-4-spiro-5'-(3'-ethyloxazolidine-2'-one),
1-methylpiperidine-4-spiro-4'-(3'-ethyloxazolidine-2'-one),
1-methylpiperidine-4-spiro-4'-(2'-methyl-2'-thiazoline),
1-methylpiperidine-4-spiro-4'(5')-(2'-methyl-2'-imidazoline),
1-methylpiperidine-4-spiro-5'-(2'-methyl-2'-oxazoline-4'-one), and their pharmaceutically acceptable salts, quaternary compounds, enantiomers and racemates.

28. A method according to claim 27, wherein said effective amount of the involved compound is comprised in a pharmaceutical composition which includes at least one pharmaceutically acceptable diluent, carrier or adjuvant.

29. A method according to claim 28, wherein said pharmaceutical composition is in a form suitable for oral, rectal, parenteral or transdermal administration, or for administration by insufflation or nasal spray.

30. A method according to claim 28, wherein said pharmaceutical composition is in a form suitable for transdermal administration and comprises as an additional component, a low molecular weight fatty acid.

31. A method according to claim 28, wherein said pharmaceutical composition is in unit dosage form.

32. A method according to claim 31, wherein said pharmaceutical composition comprises a compound in an amount in the range of about 0.5 to about 100 mg per unit dosage.

* * * * *